(12) United States Patent
Wood et al.

(10) Patent No.: US 6,414,121 B1
(45) Date of Patent: Jul. 2, 2002

(54) HUMAN KINESIN PROTEIN KSP

(75) Inventors: Kenneth W. Wood; Jeffrey T. Finer, both of Foster City; Christophe Beraud, San Francisco; John Mak, San Bruno; Roman Sakowicz, Foster City, all of CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 09/724,519

(22) Filed: Nov. 27, 2000

Related U.S. Application Data

(63) Continuation of application No. 09/592,037, filed on Jun. 12, 2000, which is a continuation of application No. 09/428,156, filed on Oct. 27, 1999.

(51) Int. Cl.[7] .............................................. C07K 14/47
(52) U.S. Cl. ........................ 530/350; 530/300; 435/183
(58) Field of Search ................................ 530/350, 300; 435/183; 536/23.1, 23.2

(56) References Cited

FOREIGN PATENT DOCUMENTS

WO    WO00/07017    2/2000

OTHER PUBLICATIONS

US Patent Application No. 09/314,464, Finer et al., Filed May 18, 1999, Title: Compositions and Assays Utilizing ADP or Phosphate for Detecting Protein Modulators.
Skolnick et al., TIBTECH 18:34–39, 2000.*
George et al., Current Methods in Sequence Comparison and Analysis, in Macromolecular Sequencing and Synthesis, Selected Methods and Applications, pp. 127–149 1988, Alan R. Liss, Inc.*
Barton, Protein Sequence Alignment and Database Scanning in Protein Structure Prediction, A Practical Approach, 1996 IRL Press at Oxford University Press, Oxford, UK, pp. 31–63.*
Blangy et al. (1995) Cell 83:1159–69, "Phosphorylation by p34cdc2 regulates spindle association of human Eg5, a kinesin–related motor essential for bipolar spindle formation in vivo".
Drummond et al. (1998) J. Cell Sci. 111:853–65 "Mutations in the bimC box of Cut7 indicate divergence of regulation within the bimC family of kinesin related proteins".
Gaglio et al. (1996) J. Cell Biol. 135:399–414 "Opposing motor activities are required for the organization of the mammalian mitotic spindle pole".
Heck et al., (1993) J. Cell Biol. 123:665–79 "The kinesin–like protein KLP61F is essential for mitosis I Drosophila".
Hoyt et al. (1992) J. Cell Biol. 118:109–120 "Two *S. cerevisae* kinesin–related gene products required for mitotic spindle assembly".

Kashina et al. (1996) Nature 379:270–2 "A bipolar kinesin".
Kashina et al. (1997) Biochim. Biophys. Acta 1357:257–71 "The bimC family of kinesins: essential bipolar mitotic driving centrosome separation".
Roof et al. (1992) J. Cell Biol. 188:95–108 "Kinesin–related proteins required for assembly of the mitotic spindle".
Sawin et al. (1992) Nature 359:540–3 "Mitotic spindle organization by a plus–end–directed microtubule motor".
Sharp et al. (1999) J. Cell Biol. 144:125–138 "The bipolar kinesin, KLP61F, cross–links microtubules within interpolar microtubule bundles of *Drosphila* embryonic mitotic spindles".
Walczak et al. (1998) Curr. Biol. 8:903–13 "A model for the proposed roles of different microtubule–based motor proteins in establishing spindle polarity".
Whitehead et al. (1998) J. Cell Sci. 111:2551–61 "Expanding the role of HsEg5 within the mitotic and post–mitotic phases of the cell cycle".
Mayer et al. (1999) Science 286:971–4 "Small molecule inhibition of mitotic spindle bipolarity identified in phenotype–based screens".
Blangy et al. (1997) J Biol Chem 272:19418–24 "Phosphorylation by p34cdc2 protein kinase regulates binding of the kinesin–related motor HsEgS5 to the dynactin subunit p150".
Blangy et al. (1998) Cell Motil Cytoskeleton 40:174–82 "Rigor–type mutation in the kinesin–related protein HsEg5 changes its subcelluar localization and induces microtubule bundling".
Crevel et al. (1997) J Mol Biol 273:160–70 "Kinetic evidence for low chemical processivity in ncd and Eg5".
Giet et al. (1999) J Biol Chem 274:15005–13 "The *Xenopus laevis* aurora–related protein kinase pEg2 associates with and phosphorylates the kinesin–related protein XIEg5".
Kapoor et al. (1999) Proc Natl Acad Sci U S A 96:9106–11 "Allele–specific activators and inhibitors for kinesin".
Lockhart et al. (1996) Biochemistry 35:2365–73 "Kinetics and motility of the Eg5 microtubule motor".
Hackney (1994) J. Biol. Chem. 269:16508–16511 "The rate–limiting step in microtubule–stimulated ATP hydrolysis by dimeric kinesin head domains occurs while bound to the microtubule".
Goldstein (1993) Annu. Rev. Genet. 27:319–351 "With apologies to Scheherazade: Tails of 1001 kinesin motors".
Desai et al. (1999) Cell 96:69–78 "Kin I kinesins are microtubule destabilizing enzymes".

(List continued on next page.)

Primary Examiner—Sheela Huff
Assistant Examiner—Larry R. Helms
(74) Attorney, Agent, or Firm—Lauren L. Stevens, Esq.; Beyer Weaver & Thomas, LLP

(57) ABSTRACT

Described herein are methods that can be used for diagnosis and prognosis of cellular proliferation. Also described herein are methods that can be used to screen candidate bioactive agents for the ability to modulate cellular proliferation. Additionally, methods and molecular targets (genes and their products) for therapeutic intervention in cancers are described.

7 Claims, 11 Drawing Sheets

OTHER PUBLICATIONS

Walczak et al. (1996) Cell 84:37–47 "XKCM1: A Xenopus kinesin–protein that regulates microtubule dynamics during mitotic spindle assembly".

Whitehead et al. (1995) GenBank Accesion No. U37426, versions 1151084 and 1171152.

Whitehead et al. (1996) Arthritis and Rheumatism 39:1635–1642 "The spindle kinesin–like protein HsEg5 is an autoantigen in systemic lupus erythematosus".

Le Guellec et al. (1991) Mol. Cell Biol. 11:3395–3398 Cloning by differential screening of a *Xenopus* cDNA that encodes a kinesin–related protein.

Cole et al. (1994) J. Biol. Chem. 269:22913–22916 "A "slow" homotetrameric kinesin–related motor protein purified from *Drosophila* embryos".

* cited by examiner

FIG. 1

```
gaattccgtc atggcgtcgc atggcgtcgc atggcgtcgc vagccaaatt cgtctgcgaa
gaagaaagag gagaagggga agaacatcca ggtggtggtg agatgcagac catttaattt
ggcagagcgg aaagctagcg cccattcaat agtagaatgt gatcctgtac gaaaagaagt
tagtgtacga actggaggat tggctgacaa gagctcaagg aaaacataca cttttgatat
ggtgtttgga gcatctacta aacagattga tgtttaccga agtgttgttt gtccaattct
ggatgaagtt attatgggct ataattgcac tatctttgcg tatggccaaa ctggcactgg
aaaaactttt acaatggaag gtgaaaggtc acctaatgaa gagtatacct gggaagagga
tcccttggct ggtataattc cacgtaccct tcatcaaatt tttgagaaac ttactgataa
tggtactgaa ttttcagtca aagtgtctct gttggagatc tataatgaag agcttttga
tcttcttaat ccatcatctg atgtttctga gagactacag atgtttgatg atccccgtaa
caagagagga gtgataatta aaggtttaga agaaattaca gtacaagaac aggatgaagt
ctatcaaatt ttagaaaagg gggcagcaaa aaggacaact gcagctactc tgatgaatgc
atactctagt cgttcccact cagtttttctc tgttacaata catatgaaag aaactacgat
tgatggagaa gagcttgtta aaatcggaaa gttgaacttg gttgatcttg caggaagtga
aaacattggc cgttctggag ctgttgataa gagagctcgg gaagctggaa atataaatca
atccctgttg actttgggaa gggtcattac tgcccttgta gaaagaacac ctcatgttcc
ttatcgagaa tctaaactaa ctagaatcct ccaggattct cttggagggc gtacaagaac
atctataatt gcaacaattt ctcctgcatc tctcaatctt gaggaaactc tgagtacatt
ggaatatgct catagagcaa agaacatatt gaataagcct gaagtgaatc agaaactcac
caaaaaagct cttattaagg agtatacgga ggagatagaa cgtttaaaac gagatcttgc
tgcagcccgt gagaaaaatg gagtgtatat ttctgaagaa aatttttagag tcatgagtgg
aaaattaact gttcaagaag agcagattgt agaattgatt gaaaaaattg gtgctgttga
ggaggagctg aatagggtta cagagttgtt tatggataat aaaaatgaac ttgaccagtg
taaatctgac ctgcaaaata aaacacaaga acttgaaacc actcaaaaac atttgcaaga
aactaaatta caacttgtta aagaagaata tatcacatca gctttggaaa gtactgagga
gaaacttcat gatgctgcca gcaagatgat taacacagtt gaagaaacta caaaagatgt
atctggtctc cattccaaac tggatcgtaa gaaggcagtt gaccaacaca atgcagaagc
tcaggatatt tttggcaaaa acctgaatag tctgtttaat aatatgaag aattaattaa
ggatggcagc tcaaagcaaa aggccatgct agaagtacat aagaccttat ttggtaatgt
gctgtcttcc agtgtctctg cattagatac cattactaca gtagcacttg gatctctcac
atctattcca gaaaatgtgt ctactcatgt ttctcagatt tttaatatga tactaaaaga
acaatcatta gcagcagaaa gtaaaactgt actacaggaa ttgattaatg tactcaagac
tgatcttcta agttcactgg aaatgatttt atccccaact gtggtgtcta tactgaaaat
caatagtcaa ctaaagcata ttttcaagac ttcattgaca gtggccgata agatagaaga
tcaaaaaaaa aggaactcag atggctttct cagtatactg tgtaacaatc tacatgaact
acaagaaaat accatttgtt ccttggttga gtcacaaaag caatgtggaa acctaactga
agacctgaag acaataaagc agacccattc ccaggaactt tgcaagttaa tgaatctttg
gacagagaga ttctgtgctt tggaggaaaa gtgtgaaaat atacagaaac cacttagtag
tgtccaggaa aatatacagc agaaatctaa ggatatagtc aacaaaatga cttttcacag
tcaaaaattt tgtgctgatt ctgatggctt ctcacaggaa ctcagaaatt ttaaccaaga
aggtacaaaa ttggttgaag aatctgtgaa acactctgat aaactcaatg gcaacctgga
aaaaatatct caagagactg aacagagatg tgaatctctg aacacaagaa cagtttattt
ttctgaacag tgggtatctt ccttaaatga aagggaacag gaacttcaca acttattgga
ggttgtaagc caatgttgtg aggcttcaag ttcagacatc actgagaaat gagatggacg
taaggcagct catgagaaac agcataacat ttttcttgat cagatgacta ttgatgaaga
taaattgata gcacaaaatc tagaacttaa tgaaaccata aaaattggtt tgactaagct
taattgcttt ctggaacagg atctgaaact ggatatccca acaggtacga caccacagag
gaaaagttat ttatacccat caacactggt aagaactgaa ccacgtgaac atctccttga
tcagctgaaa aggaaacagc ctgagctgtt aatgatgcta aactgttcag aaaacaacaa
agaagagaca attccggatg tggatgtaga agaggcagtt ctggggcagt atactgaaga
acctctaagt caagagccat ctgtagatgc tggtgtggat tgttcatcaa ttggcggggt
tccattttc cagcataaaa aatcacatgg aaaagacaaa gaaacagag gcattaacac
actggagagg tctaaagtgg actaaagtgg agagcacttg gttacaaaga gcagattacc
tctgcgagcc cagatcaacc tttaattcac ttggggggttg gcaattttat ttttaaagaa
aaacttaaaa ataaaacctg aaccccaga acttgagcct tgtgtataga ttttaaagaa
atatatatat cagccgggcg cgtggctcta gctgtaatcc cagctaactt tggaggctga
ggcgggtgga ttgcttgagc ccaggagttt gagaccagcc tggccaacgt gcgctaaaac
cttcgtctct gttaaaatt agccgggcgt ggtgggcaca ctcctgtaat cccagctact
ggggaggctg aggcacgaga atcacttgaa cccagaagcg gggttgcagt gagccaaagg
tacaccacta cactccagcc tgggcaacag agcaagactc ggtctcaaaa ataaaattta
aaaagatat aaggcagtac tgtaaattca gttgaattt gatatctacc catttttctg
tcatccctat agttcacttt gtattaaatt gggttcattt tgggatttgc aatgtaaata
           cgtatttcta gttttcatat aaagtagttc tttaggaat tc
```

FIG. 2

MASQPNSSAKKKEEKGKNIQVVVRCRPFNLAERKASAHSIVECD
PVRKEVSVRTGGLADKSSRKTYTFDMVFGASTKQIDVYRSVVCPILDEVIMGYNCTIF
AYGQTGTGKTFTMEGERSPNEEYTWEEDPLAGIIPRTLHQIFEKLTDNGTEFSVKVSL
LEIYNEELFDLLNPSSDVSERLQMFDDPRNKRGVIIKGLEEITVHNKDEVYQILEKGA
AKRTTAATLMNAYSSRSHSVFSVTIHMKETTIDGEELVKIGKLNLVDLAGSENIGRSG
AVDKRAREAGNINQSLLTLGRVITALVERTPHVPYRESKLTRILQDSLGGRTRTSIIA
TISPASLNLEETLSTLEYAHRAKNILNKPEVNQKLTKKALIKEYTEEIERLKRDLAAA
REKNGVYISEENFRVMSGKLTVQEEQIVELIEKIGAVEEELNRVTALFMDNKNELDQC
KSDLQNKTQELETTQKHLQETKLQLVKEEYITSALESTEEKLHDAASKLLNTVEETTK
DVSGLHSKLDRAKKAVDQHNAEAQDDIFGKNLSLFNNMEELIKDGSKQKAMLEVHKTL
FGNLLSSSVSALDTITTVALGSLTSIPENVSTHVSQIFNMILKEQSLAAESKTVLQEL
INVLKTDLLSSLEMILSPTVVSILKINSQLKHIFKTSLTVADKIEDQKKRNSDGFLSI
LCNNLEHELQENTICSLVESQKQCGNLTEDLKTIKQTHSQELCKLMNWTERFCALEEK
CENIQKPLSSVQENIQQKSKDIVNKMTFHSQKFCADSDGFSQELRNFNQEGTKLVEES
VKHSDKLNGNLEKISQITEQRCESLNTRTVYFSEQWVSSLNEREQELHNLLEVVSQCC
EASSSDITEKSDGRKAAHEKQHNIFLDQMTIDEDKLIAQNLELNETIKIGLTKLNCFL
EQDLKLDIPTGTTPQRKSYLYPSTLVRTEPREHLLDQLKRKQPELLMMLNCSENNKEE
TIPDVDVEEAVLGQYTEEPLSQEPSVDAGVDCSSIGGVPFFQHKKSHGKDKENRGINT
LERSKVEETTEHLVTKSRLPLRAQINL

FIG. 3

```
atggcgtgccagccaaattcgtctgcgaagaagaaagaggagaaggggaagaacatccaggtggtggtgaga
tgcagaccatttaatttggcagagcggaaagctagcgcccattcaatagtagaatgtgatcctgtacgaaaa
gaagttagtgtacgaactggaggattggctgacaagagctcaaggaaaacatacacttttgatatggtgttt
ggagcatctactaaacagattgatgtttaccgaggtgttgtttgtccaattctggatgaagttattatgggc
tataattgcactatctttgcgtatggccaaactggcactggaaaaacttttacaatggaaggtgaaggtca
cctaatgaagagtatacctgggaagaggatcccttggctggtataattccacgtacccttcatcaaattttt
gagaaacttactgataatggtactgaattttcagtcaaagtgtctctgttggagatctataatgaagagctt
tttgatcttcttaatccatcatctgatgtttctgagagactacagatgtttgatgatccccgtaacaagaga
ggagtgataattaaaggtttagaagaaattacagtacacaacaaggatgaagtgtatcaaattttagaaaag
ggggcagcaaaaaggacaactgcagctactctgatgaatgcatactctagtcgttcccactcagttttctct
gttacaatacatatgaaagaaactacgattgatggagaagagcttgttaaaatcggaaagttgaacttggtt
gatcttgcaggaagtgaaaacattggccgttctggagctgttgataagagagctcgggaagctggaaatata
aatcaatccctgttgactttgggaagggtcattactgcccttgtagaaagaacacctcatgttccttatcga
gaatctaaactaactagaatcctccaggattctcttggagggcgtacaagaacatctataattgcaacaatt
tctcctgcatctctcaatcttgaggaaactctgagtacattggaatatgctcatagagcaaagaacatattg
ctcgagggtaccgagcagaagctgatcagcgaggaggacctgatcgagcaccaccaccaccaccactga
```

FIG. 4

MACQPNSSAKKKEEKGKNIQVVVRCRPFNLAERKASAHSIVECDPVRKEVSVRTGGLADKSSRKTYTFDMVF
GASTKQIDVYRSVVCPILDEVIMGYNCTIFAYGQTGTGKTFTMEGERSPNEEYTWEEDPLAGIIPRTLHQIF
EKLTDNGTEFSVKVSLLEIYNEELFDLLNPSSDVSERLQMFDDPRNKRGVIIKGLEEITVHNKDEVYGILEK
GAAKRTTAATLMNAYSSRSHSVFSVTIHMKETTIDGEELVKIGKLNLVDLAGSENIGRSGAVDKRAREAGNI
NQSLLTLGRVITALVERTPHVPYRESKLTRILQDSLGGRTRTSIIATISPASLNLEETLSTLEYAHRAKNIL
LEQTEGKLISEEDLIEHHHHHH

FIG. 5 atggcgtgccagccaaattcgtctgcgaagaagaaagaggagaaggggaagaacatccaggtggtggtgaga
tgcagaccatttaatttggcagagcggaaagctagcgcccattcaatagtagaatgtgatcctgtacgaaaa
Gaagttagtgtacgaactggaggattggctgacaagagctcaaggaaaacatacacttttgatatggtgttt
Ggagcatctactaaacagattgatgtttaccgaggtgttgtttgtccaattctggatgaagttattatgggc
Tataattgcactatctttgcgtatggccaaactggcactggaaaaacttttacaatggaaggtgaaaggtca
Cctaatgaagagtatacctgggaagaggatcccttggctggtataattccacgtacccttcatcaaattttt
Gagaaacttactgataatggtactgaattttcagtcaaagtgtctctgttggagatctataatgaagagctt
Tttgatcttcttaatccatcatctgatgtttctgagagactacagatgtttgatgatcccgtaacaagaga
Ggagtgataattaaaggtttagaagaaattacagtacacaacaaggatgaagtgtatcaaattttagaaaag
Ggggcagcaaaaaggacaactgcagctactctgatgaatgcatactctagtcgttcccactcagttttctct
Gttacaatacatatgaaagaaactacgattgatggagaagagcttgttaaaatcggaaagttgaacttggtt
Gatcttgcaggaagtgaaaacattggccgttctggagctgttgataagagagctcgggaagctggaaatata
aatcaatccctgttgactttgggaagggtcattactgcccttgtagaaagaacacctcatgttccttatcga
gaatctaaactaactagaatcctccaggattctcttggagggcgtacaagaacatctataattgcaacaatt
tctcctgcatctctcaatcttgaggaaactctgagtacattggaatatgctcatagagcaaagaacatattg
aataagcctgaagtgaatcagaaactcaccaaaaaagctcttattaaggagtatacggaggagatagaacgt
ttaaaacgagatcttgctgcagcccgtgagaaaaatggagtgtatatttctgaagaaaattttagagtcatg
agtggaaaattaactgttcaagaagagcagattgtagaattgattgaaaaaattggtgctgttgaggaggag
ctgaatagggttacagagttgtttatggataataaaaatgaacttgaccagtgtaaatctgacctgcaaaat
aaaacacaagaacttgaaaccactcaaaaacatttgcaagaaactaaattacaacttgttaaagaagaatat
atcacatcagctttggaaagtactgaggagaaa<u>**ctcgagggtaccgagcagaagctgatcagcgaggaggac
ctgatcgagcaccaccaccaccactga**</u>

FIG. 6

MACQPNSSAKKKEEKGKNIQVVVRCRPFNLAERKASAHSIVECDPVRKEVSVRTGGLADKSSRKTYTFDMVF
GASTKQIDVYRSVVCPILDEVIMGYNCTIFAYGQTGTGKTFTMEGERSPNEEYTWEEDPLAGIIPRTLHQIF
EKLTDNGTEFSVKVSLLEIYNEELFDLLNPSSDVSERLQMFDDPRNKRGVIIKGLEEITVHNKDEVYGILEK
GAAKRTTAATLMNAYSSRSHSVFSVTIHMKETTIDGEELVKIGKLNLVDLAGSENIGRSGAVDKRAREAGNI
NQSLLTLGRVITALVERTPHVPYRESKLTRILQDSLGGRTRTSIIATISPASLNLEETLSTLEYAHRAKNIL
NKPEVNQKLTKKALIKEYTEEIERLKRDLAAAREKNGVYISEENFRVMSGKLTVQEEQIVELIEKIGAVEEE
LNRVTELFMDNKNELDQCKSDLQNKTQELETTQKHLGETKLGLVKEEYITSALESTEEKLEQTEGKLISEED
LIEHHHHHH

FIG. 7 atggcgtgccagccaaattcgtctgcgaagaagaaagaggagaaggggaagaacatccaggtggtggtgaga
tgcagaccatttaatttggcagagcggaaagctagcgcccattcaatagtagaatgtgatcctgtacgaaaa
gaagttagtgtacgaactggaggattggctgacaagagctcaaggaaaacatacacttttgatatggtgttt
ggagcatctactaaacagattgatgtttaccgaggtgttgtttgtccaattctggatgaagttattatgggc
tataattgcactatctttgcgtatggccaaactggcactggaaaaacttttacaatggaaggtgaaaggtca
cctaatgaagagtatacctgggaagaggatcccttggctggtataattccacgtaccttcatcaaattttt
gagaaacttactgataatggtactgaattttcagtcaaagtgtctctgttggagatctataatgaagagctt
tttgatcttcttaatccatcatctgatgtttctgagagactacagatgtttgatgatccccgtaacaagaga
ggagtgataattaaaggtttagaagaaattacagtacacaacaaggatgaagtgtatcaaattttagaaaag
ggggcagcaaaaaggacaactgcagctactctgatgaatgcatactctagtcgttcccactcagttttctct
gttacaatacatatgaaagaaactacgattgatggagaagagcttgttaaaatcggaaagttgaacttggtt
gatcttgcaggaagtgaaaacattggccgttctggagctgttgataagagagctcgggaagctggaaatata
aatcaatccctgttgactttgggaagggtcattactgcccttgtagaaagaacacctcatgttccttatcga
gaatctaaactaactagaatcctccaggattctcttggagggcgtacaagaacatctataattgcaacaatt
tctcctgcatctctcaatcttgaggaaactctgagtacattggaatatgctcatagagcaaagaacatattg
aataagcctgaagtgaatcagaaactcaccaaaaaagctcttattaaggagtatacggaggagatagaacgt
ttaaaacgagatcttgctgcagcccgtgagaaaaatggagtgtatatttctgaagaaaattttagagtcatg
agtggaaaattaactgttcaagaagagcagattgtagaattgattgaaaaaattggtgctgttgaggaggag
ctgaatagggttacagagttgtttatggataataaaaatgaacttgaccagtgtaaatctgacctgcaaaat
aaaacacaagaacttgaaccactcaaaaacatttgcaagaaactaaattacaacttgttaaagaagaatat
atcacatcagctttggaaagtactgaggagaaacttcatgatgctgccagcaagctgcttaacacagttgaa
gaaactacaaaagatgtatctggtctccattccaaactggatcgtaagaaggcagttgaccaacacaatgca
gaagctcaggatatttttggcaaaaacctgaatagtctgtttaataatatggaagaattaattaaggatggc
agcctcgagggtaccgagcagaagctgatcagcgaggaggacctgatcgagcaccaccaccaccaccactga

FIG. 8

MACQPNSSAKKKEEKGKNIQVVVRCRPFNLAERKASAHSIVECDPVRKEVSVRTGGLADKSSRKTYTFDMVF
GASTKQIDVYRSVVCPILDEVIMGYNCTIFAYGQTGTGKTFTMEGERSPNEEYTWEEDPLAGIIPRTLHQIF
EKLTDNGTEFSVKVSLLEIYNEELFDLLNPSSDVSERLQMFDDPRNKRGVIIKGLEEITVHNKDEVYGILEK
GAAKRTTAATLMNAYSSRSHSVFSVTIHMKETTIDGEELVKIGKLNLVDLAGSENIGRSGAVDKRAREAGNI
NQSLLTLGRVITALVERTPHVPYRESKLTRILQDSLGGRTRTSIIATISPASLNLEETLSTLEYAHRAKNIL
NKPEVNQKLTKKALIKEYTEEIERLKRDLAAAREKNGVYISEENFRVMSGKLTVQEEQIVELIEKIGAVEEE
LNRVTELFMDNKNELDQCKSDLQNKTQELETTQKHLGETKLGLVKEEYITSALESTEEKLHDAASKLLNTVE
ETTKDVSGLHSKLDRKKAVDQHNAEAQDIFGKNLNSLFNNMEELIKDGSLEQTEGKLISEEDLIEHHHHHH

FIG. 9 atgcgtgccagccaaattcgtctgcgaagaagaaagaggagaagggaagaacatccaggtggtggtgaga
tgcagaccatttaatttggcagagcggaaagctagcgcccattcaatagtagaatgtgatcctgtacgaaaa
gaagttagtgtacgaactggaggattggctgacaagagctcaaggaaaacatacacttttgatatggtgttt
ggagcatctactaaacagattgatgtttaccgaggtgttgtttgtccaattctggatgaagttattatgggc
tataattgcactatctttgcgtatggccaaactggcactggaaaaacttttacaatggaaggtgaaaggtca
cctaatgaagagtatacctgggaagaggatcccttggctggtataattccacgtacccttcatcaaattttt
gagaaacttactgataatggtactgaattttcagtcaaagtgtctctgttggagatctataatgaagagctt
tttgatcttcttaatccatcatctgatgtttctgagagactacagatgtttgatgatccccgtaacaagaga
ggagtgataattaaaggtttagaagaaattacagtacacaacaaggatgaagtgtatcaaattttagaaaag
ggggcagcaaaaaggacaactgcagctactctgatgaatgcatactctagtcgttcccactcagttttctct
gttacaatacatatgaaagaaactacgattgatggagaagagcttgttaaaatcggaaagttgaacttggtt
gatcttgcaggaagtgaaaacattggccgttctggagctgttgataagagagctcgggaagctggaaatata
aatcaatccctgttgactttgggaagggtcattactgcccttgtagaaagaacacctcatgttccttatcga
gaatctaaactaactagaatcctccaggattctcttggagggcgtacaagaacatctataattgcaacaatt
tctcctgcatctctcaatcttgaggaaactctgagtacattggaatatgctcatagagcaaagaacatattg
aataagcctgaagtgaatcagaaatag

FIG. 10

```
MACQPNSSAKKKEEKGKNIQVVVRCRPFNLAERKASAHSIVECDPVRKEVSVRTGGLADKSSRKTYTFDMVF
GASTKQIDVYRSVVCPILDEVIMGYNCTIFAYGQTGTGKTFTMEGERSPNEEYTWEEDPLAGIIPRTLHQIF
EKLTDNGTEFSVKVSLLEIYNEELFDLLNPSSDVSERLQMFDDPRNKRGVIIKGLEEITVHNKDEVYGILEK
GAAKRTTAATLMNAYSSRSHSVFSVTIHMKETTIDGEELVKIGKLNLVDLAGSENIGRSGAVDKRAREAGNI
NQSLLTLGRVITALVERTPHVPYRESKLTRILQDSLGGRTRTSIIATISPASLNLEETLSTLEYAHRAKNIL
NKPEVNQK
```

HUMAN KINESIN PROTEIN KSP

CROSS REFERENCE TO RELATED APPLICATIONS

The present invention is a continuation application of U.S. Ser. No. 09/592,037 filed Jun. 12, 2000, which is a continuation of U.S. Ser. No. 09/428,156, filed Oct. 27, 1999, both of which are incorporated herein by reference.

FIELD OF THE INVENTION

The invention relates to the use of nucleic acids encoding the kinesin KSP and their gene products to identify modulators of cell proliferation and their use in diagnosis, prognosis and treatment of cell proliferation states and disorders, for example cancer.

BACKGROUND OF THE INVENTION

Cancer is the second-leading cause of death in industrialized nations. Effective therapeutics include the taxanes and vinca alkyloids, agents which act on microtubules. Microtubules are the primary structural element of the mitotic spindle. The mitotic spindle is responsible for distribution of replicate copies of the genome to each of the two daughter cells that result from cell division. It is presumed that it is the disruption of the mitotic spindle by these drugs that results in inhibition of cancer cell division, and also induction of cancer cell death. However, microtubules also form other types of cellular structures, including tracks for intracellular transport in nerve processes. Therefore, the taxanes have side effects that limit their usefulness. Furthermore, taxanes and vinca alkaloids specifically target microtubule polymerization dynamics. There are additional dynamics of the mitotic. spindle that these compounds do not target.

Therefore, it is desirable to identify. agents and compositions which are specific and therapeutically effective against cancer. It is further desirable to identify agents and compositions which have a novel mechanism of action. It is further desirable to provide methods of diagnosis of hyper or hypo proliferation disorders. Additionally, it is desirable to identify agents and compositions which modulate cell proliferation. Cell proliferation modulation is desirable in a number of cases as discussed below, for example, for treatment of any hyper or hypo proliferation disorder, wound healing, transplantation procedures and for use in the agricultural arena. It is thus desirable to provide such methods of treatment. Moreover, it is desirable to provide assays to quickly identify such agents and compositions.

SUMMARY OF THE INVENTION

Provided herein are assays for screening for bioactive agents which affect cell proliferation. Also provided herein are methods of diagnosing proliferation states in a cell which are useful for identifying cell proliferation disorders such as cancer. Also provided are methods of prognosis and methods of treatment including treatment for cancer. As is further described below, a number of compositions and methods are provided.

In one aspect, a method of screening drug candidates is provided. In one embodiment, said method comprises providing a cell that expresses recombinant human KSP or a fragment thereof and adding a in drug candidate to said cell under conditions where the drug candidate is taken up by the cell. The method further includes determining the effect of said drug candidate on the bioactivity of said recombinant human KSP. The bioactivity of recombinant human KSP, or particularly the changes in the presence of a drug candidate, can be determined by assays such as those for determining cellular proliferation, cellular viability, and cellular morphology. In a further aspect of the invention, any changes in bioactivity of recombinant human KSP can be determined by assays for determining changes in the mitotic spindle, particularly inhibition of mitosis, and ATP hydrolysis. The methods herein may also determine the bioactivity of recombinant human KSP in the presence and absence of candidate agents by performing assays determining the effect on apoptosis and necrosis.

The methods provided herein can be performed on single individual cells or a population of cells. The cell can be any kind of cell including but not limited to a lymphocyte, cancer cell or an endothelial cell. In one aspect), wherein cancer cells are utilized, cancer growth or inhibition can be determined, and wherein endothelial cells are utilized, angiogenesis or inhibition thereof can be determined.

In another aspect of the invention, a method of screening for a bioactive agent capable of binding to a cellular proliferation protein is provided. Preferably, the cellular proliferation protein is human KSP or a fragment thereof. In one embodiment, said method comprises combining said cellular proliferation protein and a candidate bioactive agent, wherein said candidate bioactive agent is an exogenous agent, and determining the binding of said candidate agent to said cellular proliferation protein.

In a further aspect herein, a method of screening for a candidate protein capable of binding to a cellular proliferation protein, wherein said cellular proliferation protein is KSP or a fragment thereof, is provided. In a preferred method, said method comprises combining a nucleic acid encoding said cellular proliferation protein and a nucleic acid encoding a candidate protein, wherein an identifiable marker is expressed wherein said candidate protein binds to said cellular proliferation protein.

Also provided herein is a method for screening for a bioactive agent capable of interfering with the binding of a cellular proliferation protein, wherein said cellular proliferation protein is KSP or a fragment thereof, and an antibody which binds to said cellular proliferation protein. In one embodiment, the method comprises combining a cellular proliferation protein, wherein said cellular proliferation protein is KSP or fragment thereof, a candidate bioactive agent and an antibody which binds to said cellular proliferation protein and determining the binding of said cellular proliferation protein and said antibody.

In a further aspect of the invention herein, a method for screening for a bioactive agent capable of modulating the activity of a cellular proliferation protein, wherein said cellular proliferation protein is human KSP or a fragment thereof, is provided. In one aspect, said method comprises combining said cellular proliferation protein and a candidate bioactive agent, wherein said candidate bioactive agent is an exogenous agent, and determining the effect of said candidate agent on the activity of said cellular proliferation protein.

Also provided herein is a method of screening drug candidates comprising providing a cell that expresses KSP, adding a drug candidate to said cell, and determining the effect of said drug candidate on the expression of KSP. In a further aspect the method includes comparing the level of expression in the absence of said drug candidate to the level of expression in the presence of said drug candidate, wherein the concentration of said drug candidate can vary when present, and wherein said comparison can occur after addition or removal of the drug candidate. In a preferred embodiment, the expression of said KSP is decreased as a result of the introduction of the drug candidate. Preferably, the cell utilized is a tumor cell.

In a further aspect, a method of evaluating the effect of a candidate drug on cellular proliferation (a candidate cellular proliferation drug) is provided which comprises administering said drug to a patient, removing a cell sample from said patient, and determining the expression profile of said cell, wherein said expression profile includes a KSP gene. In another aspect, the method includes comparing said expression profile to an expression profile of a healthy individual.

In another aspect herein, a method of diagnosing a hyper-proliferative disorder in an individual is provided herein comprising determining the level of expression a KSP gene in an individual and comparing said level to a standard or control level of expression, wherein an increase indicates that the individual has a hyper-proliferative disorder, such as, but not limited to, cancer.

Also provided herein is a method of evaluating the effect of a candidate cellular proliferation drug comprising administering said drug to a patient wherein said patient has cancer and has been identified as expressing KSP at a level higher than an individual not having cancer, removing a cell sample from said patient, and determining the effect on KSP activity, wherein said KSP activity is mitosis.

In the methods provided herein, the cells can come from a variety of sources. For example, samples can be from, but are not limited to, a blood sample, a urine sample, a buccal sample, a PAP smear, cerebral spinal fluid, and any tissue including, breast tissue, lung tissue and colon tissue. In one embodiment, the patient has cancer.

Also provided herein is a method for inhibiting cellular proliferation, said method comprising administering to a cell a composition comprising an antibody to KSP, wherein said antibody is conjugated to a ligand. In one aspect, the ligand of the antibody is tumor cell specific. In another aspect, the ligand facilitates said antibody entry to said cell. Moreover, the antibody can be a humanized antibody. The methods of inhibition can be performed in vitro on cells or in vivo on an individual. In one embodiment, the cells are cancerous. In a further embodiment, the individual has cancer. Another method of inhibiting cellular proliferation in a cell or individual is provided herein which comprises administering to a cell or individual a composition comprising antisense molecules to KSP.

In yet another embodiment herein, a method for inhibiting cellular proliferation is provided which comprises administering to a cell a composition comprising an inhibitor of KSP. In one embodiment the inhibitor is of human KSP or a fragment thereof. In one embodiment, the inhibitor is specific to human KSP. In one embodiment, KSP inhibitors are any agent which disrupts or inhibits KSP activity as further described herein. In one aspect of the invention, the inhibitor of KSP is a small molecule as further defined herein. Generally, small molecules have a molecular weight of between 50 kD and 2000 kD, and in some cases, less than 1500 kD, or less than 1000 kD, or less than 500 kD. Examples of KSP inhibitors include but are not limited to small molecules, ribozymes, antisense molecules, and antibodies. KSP inhibitors are further described herein and in the application filed Oct. 27, 1999; entitled Methods and Compositions Utilizing Quinazolinones (U.S. Ser. No. 60/198, 253, namned inventor Jeffrey T. Finer), incorporated by reference in its entirety. The composition which is administered to a cell further comprises an acceptable pharmaceutical carrier in one embodiment. The composition can have a variety of formulations, including, but not limited to those for parental, oral or topical administration.

The methods of inhibiting cellular proliferation can be performed in vitro or in vivo. More particularly, the compositions can be administered to cells in vitro or in an individual. The individual may have a disease or be at risk for disease. Disease states which can be treated by the methods herein are further described below. In one case, the individual has cancer or is at risk for restenosis. The cell can be any cell, preferably a cancer cell. Other preferred cell types include but are not limited to endothelial cells and metastatic cancer cells. In one embodiment,.the method of inhibiting by the KSP inhibitor is by disruption of mitosis or induction of apoptosis.

In a further aspect of the invention, a biochip comprising a nucleic acid segment from KSP, wherein said biochip comprises fewer than 1000 nucleic acid probes, is provided. Methods of screening and diagnosing conditions with said biochip are also provided herein.

Other aspects of the invention will become apparent to the skilled artisan by the following description of the invention.

DETAILED DESCRIPTION OF THE FIGURES

FIG. 1 shows a cDNA sequence for human KSP (SEQ ID NO: 1), GenBank accession number X85137, wherein the start and stop codons are shown underlined and in bold, beginning at positions 11 and 3182, respectively.

FIG. 2 shows an amino acid sequence encoding human KSP (SEQ ID NO: 2).

Figure 11:
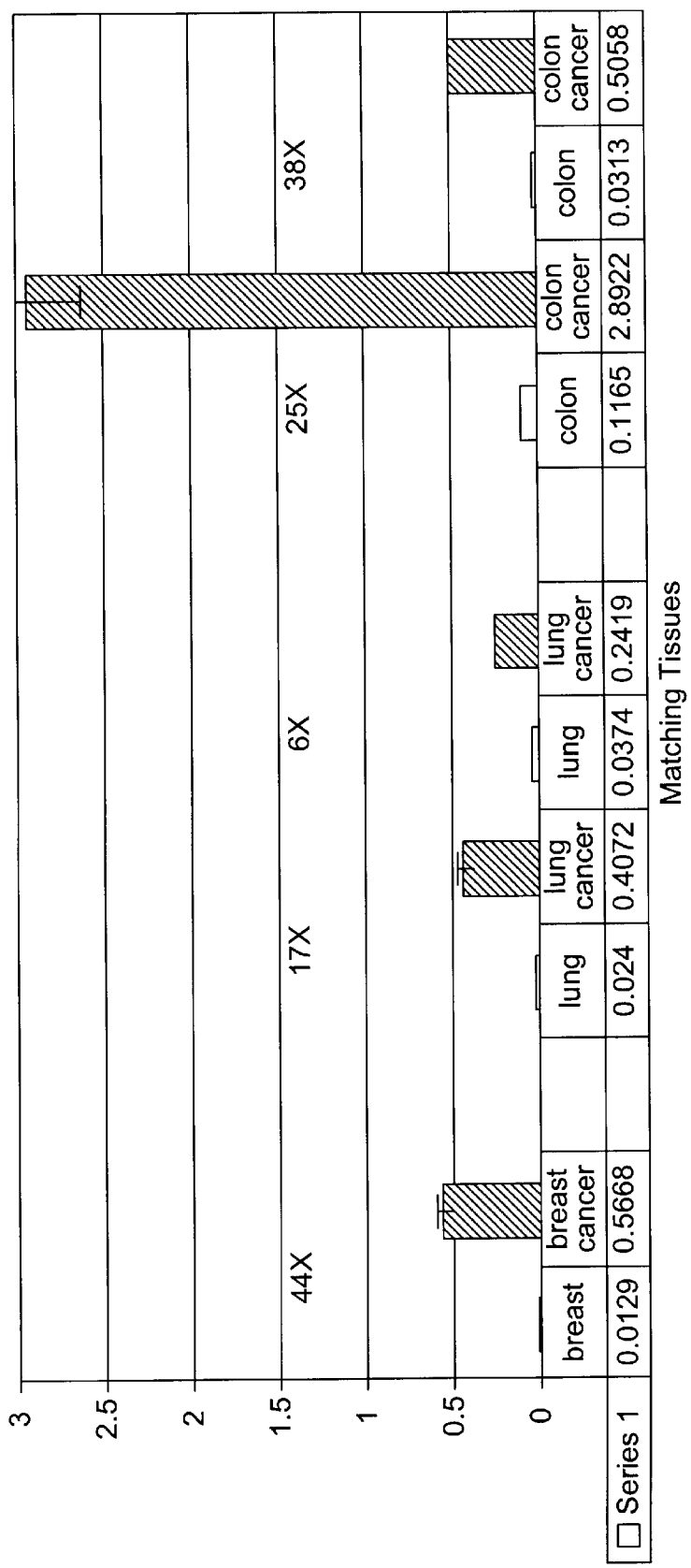

FIG. 3 shows a nucleic acid sequence encoding a fragment of KSP (SEQ ID NO:3), termed KSPL360 herein. Portions differing from the sequences of FIGS. 1 and 2 are indicated in bold typeface and are underlined. Residues at the C-terminus include a myc epitope and a 6-histidine tag.

FIG. 4 shows an amino acid sequence encoding KSPL360 (SEQ ID NO: 4).

FIG. 5 shows a nucleic acid sequence encoding a fragment of KSP (SEQ ID NO: 5), termed KSP-K491 herein. Portions differing from the sequences of FIGS. 1 and 2 are indicated in bold typeface and are underlined. Residues at the C-terminus include a myc epitope and a 6-histidine tag.

FIG. 6 shows an amino acid sequence encoding KSP-K491 (SEQ ID NO: 6).

FIG. 7 shows a nucleic acid sequence encoding a fragment of KSP (SEQ ID NO: 7), termed KSP-S553 herein. Portions differing from the sequences of FIGS. 1 and 2 are indicated in bold typeface and are underlined. Residues at the C-terminus include a myc epitope and a 6-histidine tag.

FIG. 8 shows an amino acid sequence encoding KSP-S553 (SEQ ID NO: 8).

FIG. 9 shows a nucleic acid sequence encoding a fragment of KSP (SEQ ID NO: 9), termed KSP-K368 herein. Portions differing from the sequences of FIGS. 1 and 2 are indicated in bold typeface and are underlined.

FIG. 10 shows an amino acid sequence encoding KSP-K368 (SEQ ID NO: 10).

FIG. 11 is a graph showing KSP mRNA levels in matched normal and tumor tissue from breast, lung and colon. MRNA levels were measured by quantitative PCR relative to a standard. The relative magnitudes of overexpression in each tumor sample relative to the matched normal tissue are displayed above each pair. All values are normalized to the level of KSP mRNA expression observed in cultured HeLa cells.

DETAILED DESCRIPTION OF THE INVENTION

Provided herein are assays for screening for bioactive agents which affect cell proliferation. Also provided herein are methods of diagnosing proliferation states in a cell which are useful for identifying cell proliferation disorders such as cancer. Also provided are methods of prognosis and methods of treatment including treatment for cancer. As is further described below, a number of compositions and methods are provided.

In one aspect, the assays or methods of diagnosis provided herein include the use of a cellular proliferation protein or nucleic acid. The terms "cell proliferation" and "cellular proliferation" are used herein interchangeably. Additionally, the cellular proliferation protein and nucleic acid can be referred to herein as "cellular proliferation sequences" wherein the context will indicate whether the sequence is an amino acid sequence, nucleic acid sequence, or either.

In a preferred embodiment, the cellular proliferation sequence is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibody directed against KSP into cells prevents spindle pole separation during prometaphase, giving rise to monopolar spindles and causing mitotic arrest. KSP and related kinesins bundle antiparallel microtubules and slide them relative to one another, thus forcing the two spindle poles apart. KSP may also mediate in anaphase B spindle elongation and focussing of microtubules at the spindle pole.

Human KSP has been reported on (also termed HsEg5). Galgio, et al., J. Cell Biol., 135(2):399–414 (1996); Kaiser, et al., JBC, 274(27):18925–31 (1999); Blangy, et al., Cell, 83:1159–69 (1995); Blangy, et al., J Biol Chem., 272:19418–24 (1997); Blangy, et al., Cell Motil Cytoskeleton, 40:174–82 (1998); Whitehead, et al., Arthritis Rheum., 39:1635–42 (1996); GenBank accession numbers: X85137, NM_004523 and U37426. Moreover, a fragment of the KSP gene (TRIP5) has been reported on. Lee, et al., Mol Endocrinol., 9:243–54 (1995); GenBank accession number L40372. Also see, Whitehead and Rattner, J. Cell Sci., 111:2551–61 (1998).

Xenopus KSP homologs (Eg5) have also been reported on. Walczak, et al., Curr Biol., 8(16):903–13 (1998); Le Guellec, et al., Mol. Cell Biol., 11 (6):3395–8 (1991); Sawin, et al., Nature, 359:540–3 (1992); Sawin and Mitchison, Mol. Biol Cell, 5:217–26 (1994); Sawin and Mitchison, PNAS, 92:4289–93 (1995); Kapoor and Mitchison, PNAS, 96:9106–11 (1999); Lockhart and Cross, Biochemistry, 35(7):2365–73 (1996); Crevel, et al, J. Mol. Biol., 273:160–170 (1997). Additionally, Drosophila KLP61 F/KRP130 has been reported on. Heck, et al., J Cell Biol, 123:665–79 (1993); Cole, et al., J. Biol. Chem., 269(37):22913–6 (1994); Barton, et al., Mol. Biol. Cell, 6:1563–74 (1995).

In the preferred embodiment herein, a sequence as shown in the figures is utilized. As indicated herein, in some embodiments a fragment of KSP is utilized. Preferred protein fragments are shown in FIGS. 2, 4, 6, and 8. In one embodiment, the cellular proliferation fragment shown in FIG. 4 is preferred. Preferred fragments of KSP have kinesin activity as further described below. Moreover, in one embodiment, KSP peptides or fragments have at least one, and preferably at least two epitope tags. In a preferred embodiment, a KSP fragment comprises a myc epitope and a histidine tag.

In another preferred embodiment herein, the cellular proliferation protein is non-glycosylated. For example, in one embodiment the protein is, for example, human, expressed in bacteria, for example, E. Coli. Moreover, phosphorylation and/or methylation of KSP as used herein may differ from KSP as found in its native form within a cell.

Thus, while it is preferred that the cellular proliferation sequences are from humans, sequences from other organisms may be useful in animal models of disease and drug evaluation; thus, in alternative embodiments, other sequences are provided such as from vertebrates, including mammals, including rodents (rats, mice, hamsters, guinea pigs, etc.), primates, farm animals (including sheep, goats, pigs, cows, horses, etc), Xenopus, and Drosophila.

In another embodiment, the sequences are naturally-occurring allelic variants of the sequences set forth in the figures. In another embodiment, the sequences are sequence variants as further described herein.

In one embodiment, a cellular proliferation sequence can be initially identified by substantial nucleic acid and/or amino acid sequence homology to the cellular proliferation sequences outlined herein. Such homology can be based upon the overall nucleic acid or amino acid sequence, and is generally determined as outlined below, using either homology programs or hybridization conditions.

Thus, in one embodiment, a nucleic acid is a "cellular proliferation nucleic acid" if the overall homology of the nucleic acid sequence to the nucleic acid sequences of FIGS. 1, 3, 5, 7 or 9 (the nucleic acid figures) is preferably greater than about 75%, more preferably greater than about 80%, even more preferably greater than about 85% and most preferably greater than 90%. In some embodiments the homology will be as high as about 93 to 95 or 98%. Homology as used herein is in reference to sequence similarity or identity, with identity being preferred. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387–395 (1984), preferably using the default settings, or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mole. Biol. 215, 403–410, (1990) and Karlin et al., PNAS USA 90:5873–5787 (1993). A particularly useful BLAST program is the WU-BLAST-2 program which was obtained from Altschul et al., Methods in Enzymology, 266:460480 (1996). WU-BLAST-2 uses several search parameters, most of which are set to the default values. The adjustable parameters are set with the following values: overlap span=1, overlap fraction=0.125, word threshold (T)=11. The HSP S and RSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the sequence shown in the nucleic acid figures. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of the nucleic acid figures, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

In one embodiment, the cellular proliferation nucleic acid is determined through hybridization studies. Thus, for example, nucleic acids which hybridize under high stringency to the nucleic acid sequences identified in the figures, or a complement, are considered a cellular proliferation sequence in one embodiment herein. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

In addition, in one embodiment the cellular proliferation nucleic acid sequences of the invention are fragments of larger genes, i.e. they are nucleic acid segments. "Genes" in this context includes coding regions, non-coding regions, and mixtures of coding and non-coding regions. Accordingly, as will be appreciated by those in the art, using the sequences provided herein, additional sequences of the cellular proliferation genes can be obtained, using techniques well known in the art for cloning either longer sequences or the full length sequences; see Maniatis et al., and Ausubel, et al., supra, hereby expressly incorporated by reference.

Once the cellular proliferation nucleic acid is identified, it can be cloned and, if necessary, its constituent parts recombined to form the entire cellular proliferation nucleic acid. Once isolated from its natural source, e.g., contained within a plasmid or other vector or excised therefrom as a linear nucleic acid segment, the recombinant cellular proliferation nucleic acid can be further-used as a probe to identify and isolate other cellular proliferation nucleic acids, for example additional coding regions. It can also be used as a "precursor" nucleic acid to make modified or variant cellular proliferation nucleic acids and proteins. "Recombinant" as used herein refers to a nucleic acid or protein which is not in its native state. For example, the nucleic acid can be genetically engineered, isolated, inserted into a man-made vector or be in a cell wherein it is not natively expressed in order to be considered recombinant.

In another aspect, the cellular proliferation nucleic acid and protein sequences are differentially expressed in cells having varying states of cellular proliferation, including cancer cells which over proliferate compared to non cancerous cells. As outlined below, cellular proliferation sequences include those that are up-regulated (i.e. expressed at a higher level) during cellular proliferation, as well as those that are down-regulated (i.e. expressed at a lower level) in cellular proliferation. In a preferred embodiment, the cellular proliferation sequences are upregulated during cellular proliferation in their native state, ie., without the administration of modulators or therapeutics.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605–2608 (1985); Cassol et al., 1992; Rossolini et al., Mol. Cell. Probes 8:91–98 (1994)). The term nucleic acid is used interchangeably with gene, cDNA, and mRNA encoded by a gene.

The cellular proliferation nucleic acids of the present invention are used in several ways. In a preferred embodiment, cellular proliferation nucleic acids encoding cellular proliferation proteins are used to make a variety of expression vectors to express cellular proliferation proteins which can then be used in screening assays, as described below. The expression vectors may be either self-replicating extrachromosomal vectors or vectors which integrate into a host genome. Generally, these expression vectors include transcriptional and translational regulatory nucleic acid operably linked to the nucleic acid encoding the cellular proliferation protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide;

a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the cellular proliferation protein; for example, transcriptional and translational regulatory nucleic acid sequences from Bacillus are preferably used to express the cellular proliferation protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The cellular proliferation proteins of the present invention can be produced by culturing a host cell transformed with an expression vector containing nucleic acid encoding a cellular proliferation protein, under the appropriate conditions to induce or cause expression of the cellular proliferation protein. The conditions appropriate for cellular proliferation protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are Drosophila melangaster cells, *Saccharomyces cerevisiae* and other yeasts, *E. coli, Bacillus subtilis*, Sf9 cells, C129 cells, 293 cells, Neurospora, BHK, CHO, COS, HeLa cells, THP1 cell line (a macrophage cell line) and human cells and cell lines.

In one embodiment, the cellular proliferation proteins are expressed in mammalian cells. Mammalian expression systems are also known in the art, and include retroviral systems. A preferred expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, cellular proliferation proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the cellular proliferation protein in bacteria. The protein is either secreted into the growth media (gram-positive bacteria) or into the periplasmic space, located between the inner and outer membrane of the cell (gram-negative bacteria). The expression vector may also include an epitope tag providing for affinity purification of the cellular proliferation protein. The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In one embodiment, cellular proliferation proteins are produced in insect cells. Expression vectors for the transformation of insect cells, and in particular, baculovirus-based expression vectors, are well known in the art.

In another, embodiment, cellular proliferation protein is produced in yeast cells. Yeast expression systems are well known in the art, and include expression vectors for Saccharomyces cerevisiae, *Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

The cellular proliferation protein may also be made as a fusion protein, using techniques well known in the art. Thus, for example, for the creation of monoclonal antibodies, if the desired epitope is small, the cellular proliferation protein may be fused to a carrier protein to form an immunogen. Alternatively, the cellular proliferation protein may be made as a fusion protein to increase expression, or for other reasons. For example, when the cellular proliferation protein is a cellular proliferation peptide, the nucleic acid encoding the peptide may be linked to other nucleic acid for expression purposes.

In one embodiment, the cellular proliferation nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the cellular proliferation nucleic acids, proteins and antibodies at any position. For example, the label should be capable of producing, either directly or indirectly, a detectable signal. The detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Accordingly, the present invention also provides cellular proliferation protein sequences. A cellular proliferation protein of the present invention may be identified in several ways. "Protein" in this sense includes proteins, polypeptides, and peptides. As will be appreciated by those in the art, the nucleic acid sequences of the invention can be used to generate protein sequences.

Also included within one embodiment of cellular proliferation proteins are amino acid variants of the naturally occurring sequences, as determined herein. Preferably, the variants are preferably greater than about 75% homologous to the wild-type sequence, more preferably greater than about 80%, even more preferably greater than about 85% and most preferably greater than 90%. In some embodiments the homology will be as high as about 93 to 95 or 98%. As for nucleic acids, homology in this context means sequence similarity or identity, with identity being preferred. This homology will be determined using standard techniques known in the art as are outlined above for the nucleic acid homologies. The proteins of the present invention may be shorter or longer than the wild type amino acid sequences. Thus, in a preferred embodiment, included within the definition of cellular proliferation proteins are portions or fragments of the wild type sequences. Preferred fragments have a binding domain to a modulating agent or antibody as discussed below. In addition, as outlined above, the cellular proliferation nucleic acids of the invention may be used to obtain additional coding regions, and thus additional protein sequence, using techniques known in the art.

In one embodiment, the cellular proliferation proteins are derivative or variant cellular proliferation proteins as compared to the wild-type sequence. That is, as outlined more fully below, the derivative cellular proliferation peptide will contain at least one amino acid substitution, deletion or insertion, with amino acid substitutions being particularly preferred. The amino acid substitution, insertion or deletion or combination thereof may occur at any residue within the cellular proliferation peptide. These variants ordinarily are prepared by site specific mutagenesis of nucleotides in the DNA encoding the cellular proliferation protein, using cassette or PCR mutagenesis or other techniques well known in the art, to produce DNA encoding the variant, and thereafter expressing the DNA in recombinant cell culture as outlined above. However, variant cellular proliferation protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the cellular proliferation protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed cellular proliferation variants screened for the optimal combination of desired activity. Techniques for making substitution mutations at predetermined sites in DNA having a known sequence are well known, for example, M13 primer mutagenesis and PCR mutagenesis. Screening of the mutants is done using assays of cellular proliferation protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the cellular proliferation protein are desired, substitutions are generally made in accordance with the following chart:

Chart 1

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the cellular proliferation proteins as needed. Alternatively, the variant may be designed such that the biological activity of the cellular proliferation protein is altered.

Covalent modifications of cellular proliferation polypeptides are included within the scope of this invention. One type of covalent modification includes reacting targeted amino acid residues of a cellular proliferation polypeptide with an organic derivatizing agent that is capable of reacting with selected side chains or the N- or C-terminal residues of a cellular proliferation polypeptide. Derivatization with bifunctional agents is useful, for instance, for crosslinking cellular proliferation protein to a water-insoluble support matrix or surface for use in the method for purifying anti-KSP antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the α-amino groups of lysine, arginine, and histidine side chains [T. E. Creighton, Proteins: Structure and Molecular Properties, W.H. Freeman & Co., San Francisco, pp. 79–86 (1983)], acetylation of the N-terminal amine, and amidation of any C-terminal carboxyl group.

Another type of covalent modification of the cellular proliferation polypeptide included within the scope of this invention comprises altering the native glycosylation pattern of the polypeptide. "Altering the native glycosylation pattern" is intended for purposes herein to mean deleting one or more carbohydrate moieties found in native sequence cellular proliferation polypeptide, and/or adding one or more glycosylation sites that are not present in the native sequence cellular proliferation polypeptide.

Addition of glycosylation sites to cellular proliferation polypeptides may be accomplished by altering the amino acid sequence thereof. The alteration may be made, for example, by the addition of, or substitution by, one or more serine or threonine residues to the native sequence cellular proliferation polypeptide (for O-linked glycosylation sites). The cellular proliferation amino acid sequence may optionally be altered through changes at the DNA level, particularly by mutating the DNA encoding the cellular proliferation polypeptide at preselected bases such that codons are generated that will translate into the desired amino acids.

Another means of increasing the number of carbohydrate moieties on the cellular proliferation polypeptide is by chemical or enzymatic coupling of glycosides to the polypeptide. Such methods are described in the art, e.g., in WO 87/05330 published Sep. 11, 1987, and in Aplin and Wriston, cellular proliferation Crit. Rev. Biochem., pp. 259–306 (1981).

Removal of carbohydrate moieties present on the cellular proliferation polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of cellular proliferation comprises linking the cellular proliferation polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The cellular proliferation polypeptides of the present invention may also be modified in one embodiment in a way to form chimeric molecules comprising a cellular proliferation polypeptide fused to another, heterologous polypeptide or amino acid sequence. In one embodiment, such a chimeric molecule comprises a fusion of a cellular proliferation polypeptide with a tag polypeptide which provides an epitope to which an anti-tag antibody can selectively bind. Preferred tags include the myc epitope and 6-histidine. The epitope tag is generally placed at the amino-or carboxyl-terminus of the cellular proliferation polypeptide. The presence of such epitope-tagged forms of a cellular proliferation polypeptide can be detected using an antibody against the tag polypeptide as further discussed below. Also, provision of the epitope tag enables the cellular proliferation polypeptide to be readily purified by affinity purification using an anti-tag antibody or another type of affinity matrix that binds to the epitope tag. In an alternative embodiment, the chimeric molecule may comprise a fusion of a cellular proliferation polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

Also included with the definition of cellular proliferation protein in one embodiment are other cellular proliferation proteins of the cellular proliferation family, and cellular proliferation proteins from other organisms, which are cloned and expressed as outlined below Thus, probe or degenerate polymerase chain reaction (PCeR) primer sequences may be used to find other related cellular proliferation proteins from humans or other organisms. As will be appreciated by those in the art, particularly useful probe and/or PCR primer sequences include the unique areas of the cellular proliferation nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art.

In addition, as is outlined herein, cellular proliferation proteins can be made that are longer than those depicted in the figures, for example, by the elucidation of additional sequences, the addition of epitope or purification tags, the addition of other fusion sequences, etc.

Cellular proliferation proteins may also be identified as being encoded by cellular proliferation nucleic acids. Thus, in one embodiment, cellular proliferation proteins are encoded by nucleic acids that will hybridize to the sequences of the nucleic acid figures, or their complements, as outlined herein.

In a preferred embodiment, the cellular proliferation protein is purified or isolated after expression. 15 Cellular proliferation proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the cellular proliferation protein may be purified using a standard anti-KSP antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the cellular proliferation protein. In some instances no purification will be necessary.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure. In a preferred embodiment, a protein is considered pure wherein it is determined that there is no contaminating activity.

Once expressed and purified if necessary, the cellular proliferation proteins and nucleic acids are useful in a number of applications. In a number of methods provided herein, wherein either the nucleic acid or a protein is used, a candidate bioactive agent is used to determine the effect on the cellular proliferation sequence, cellular proliferation, cancer, etc., as further discussed below.

In preferred embodiments, the bioactive agents modulate the cellular proliferation sequences or expression profiles provided herein. In a particularly preferred embodiment, the candidate agent suppresses a cellular proliferation phenotype, for example to inhibit proliferation, inhibit tumor growth, or to a normal tissue fingerprint as further discussed below. Similarly, the candidate agent preferably suppresses a severe cellular proliferation phenotype. Suppression might take the form of cell or tumor growth arrest, with continued viability. Alternatively, suppression may take the form of inducing cell death of cells, thereby eliminating proliferation. As further discussed below, preferred bioactive agents are identified which cause cell death selectively of tumor cells or proliferating cells. Generally a plurality of assay mixtures are run in parallel with different agent concentrations to obtain a differential response to the various concentrations. Typically, one of these concentrations serves as a negative control, i.e., at zero concentration or below the level of detection.

The term "candidate bioactive agent" or "drug candidate" or grammatical equivalents as used herein describes any molecule, e.g., protein, oligopeptide, small organic molecule, polysaccharide, polynucleotide, purine analog, etc., to be tested for bioactive agents that are capable of directly or indirectly altering either the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, preferred embodiments exclude molecules already known to bind to that particular protein, for example, polymer structures such as microtubules, and energy sources such as ATP. Preferred embodiments of assays herein include candidate agents which do not bind the cellular proliferation protein in its endogenous native state termed herein as "exogenous" agents. In another preferred embodiment, exogenous agents further exclude antibodies to KSP.

Candidate agents can encompass numerous chemical classes, though typically they are organic molecules, preferably small organic compounds having a molecular weight of more than 100 and less than about 2,500 daltons. Small molecules are further defined herein as having a molecular weight of between 50 kD and 2000 kD. In another embodiment, small molecules have a molecular weight of less than 1500, or less than 1200, or less than 1000, or less than 750, or less than 500 kD. In one embodiment, a small molecule as used herein has a molecular weight of about 100 to 200 kD. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "arbohydrate Modifications in Antisense Research", Ed. Y.S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y.S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News June 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

In a preferred embodiment, as outlined above, screens may be done on individual genes and gene products (proteins). In a preferred embodiment, the gene or protein has been identified as described below as a differentially expressed gene important in a particular state. Thus, in one embodiment, screens are designed to first find candidate agents that can bind to differentially expressed proteins, and then these agents may be used in assays that evaluate the ability of the candidate agent to modulate differentially expressed activity. Thus, as will be appreciated by those in the art, there are a number of different assays which may be run; binding assays and activity assays.

In a preferred embodiment, binding assays are provided. In one embodiment, the methods comprise combining a cellular proliferation protein and a candidate bioactive agent in the presence or absence of microtubules, and determining the binding of the candidate agent to the cellular proliferation protein. Preferred embodiments utilize the human cellular proliferation protein, although other mammalian proteins may also be used as discussed above, for example for the development of animal models of human disease. In some embodiments, as outlined herein, variant or derivative cellular proliferation proteins may be used.

Generally, in a preferred embodiment of the methods herein, the cellular proliferation protein or the candidate agent is non-diffusably bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflontm, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In a preferred embodiment, the cellular proliferation protein is bound to the support, and, in the presence or absence of microtubules, a candidate bioactive agent is added to the assay. Alternatively, the candidate agent is bound to the support and the cellular proliferation protein is added. Novel binding agents include specific antibodies, non-natural binding agents identified in screens of chemical libraries, peptide analogs, etc. A wide variety of assays may be used for this purpose, including labeled in vitro protein-protein binding assays, electrophoretic mobility shift assays, immunoassays for protein binding, functional assays (phosphorylation assays, etc.) and the like.

Moreover, in another aspect, screening assays are performed herein where neither the drug candidate nor cellular proliferation protein are bound to a solid support. Soluble assays are known in the art. In one embodiment, binding of a cellular proliferation protein, or fragment thereof, to a drug candidate can be determined by changes in fluorescence of either the cellular proliferation protein or the drug candidate, or both. Fluorescence may be intrinsic or conferred by labeling either component with a fluorophor. As an example that is not meant to be limiting, binding could be detected by fluorescence polarization.

The determination of the binding of the candidate bioactive agent to the cellular proliferation protein may be done in a number of ways. In a preferred embodiment, the candidate bioactive agent is labelled, and binding determined directly. For example, this may be done by attaching all or a portion of the cellular proliferation protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorofers including organo-metallic fluorescent compounds, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. cellular proliferation protein), such as ATP, microtubules, an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the cellular proliferation protein and thus is capable of binding to, and potentially modulating, the activity of the cellular proliferation protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the cellular proliferation protein with a higher affinity. Thus, if the candidate bioactive agent is labeled, the presence of the label on the support, coupled with a lack of competitor binding, may indicate that the candidate agent is capable of binding to the cellular proliferation protein.

In another aspect herein, proteins which bind to KSP or a fragment thereof are identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463.

In a preferred embodiment, the binding site of the cellular proliferation protein is identified and provided herein. This can be done in a variety of ways. For example, once the cellular proliferation protein has been identified as binding to a bioactive agent, the protein is fragmented or modified and the assays repeated to identify the necessary components for binding.

In a preferred embodiment, the methods comprise differential screening to identify bioactive agents that are capable of modulating the activity of the cellular proliferation proteins. In this embodiment, the methods comprise combining a cellular proliferation protein and a competitor in a first sample. A second sample comprises a candidate bioactive agent, a cellular proliferation protein and a competitor. The binding of the competitor is determined for both samples, and a change, or difference in binding between the two samples indicates the presence of an agent capable of binding to the cellular proliferation protein and, in one embodiment, modulating its activity. Methods of determining modulation of activity are further described below. That is, if the binding of the competitor is different in the second sample relative to the first sample, the agent is capable of binding to the cellular proliferation protein.

Alternatively, a preferred embodiment utilizes differential screening to identify drug candidates that, in the presence or absence of microtubules, bind to the native cellular proliferation protein, but cannot bind to modified cellular proliferation proteins. The structure of the cellular proliferation protein may be modeled, and used in rational drug design to synthesize agents that interact with that site. Drug candidates that affect cellular proliferation bioactivity are also identified by screening drugs for the ability to either enhance or reduce the activity of the protein in the presence or absence of microtubules.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radio label is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce nonspecific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of cellular proliferation proteins may also be done. In a preferred embodiment, methods for screening for a bioactive agent capable of modulating the activity of cellular proliferation proteins comprise the steps of adding a candidate bioactive agent to a sample of cellular proliferation proteins in the presence or absence of microtubules, as above, and determining an alteration in the biological activity of cellular proliferation proteins. "Modulating the activity of cellular proliferation" includes an increase in activity, a decrease in activity, or a change in the type or kind of activity present. Thus, in this embodiment, the candidate agent should both bind to cellular proliferation proteins (although this may not be necessary), and alter its biological or biochemical activity as defined herein. The methods include both in vitro screening methods, as are generally outlined above, and in vivo screening of cells for alterations in the presence, distribution, activity or amount of cellular proliferation proteins.

Thus, in this embodiment, the methods comprise combining a cellular proliferation sample and a candidate bioactive agent, and evaluating the effect on cellular proliferation activity. By "cellular proliferation protein activity" or grammatical equivalents herein is meant at least one of the cellular proliferation protein's biological activities, including, but not limited to, kinesin activity, regulation of spindle pole separation, mitosis, mitotic spindle assembly, satisfaction of the mitotic cell cycle checkpoint, cell cycle progression, apoptosis, cell proliferation, mitotic and involvement in tumor growth. An inhibitor of cellular proliferation activity is the inhibition of any one or more cellular proliferation protein activities.

Kinesin activity is known in the art and includes one or more kinesin activities. Kinesin activities include the ability to affect ATP hydrolysis, microtubule binding, gliding and polymerization/depolymerization (effects on microtubule dynamics), binding to other proteins of the spindle, binding to proteins involved in cell-cycle control, or serving as a substrate to other enzymes, such as kinases or proteases and specific kinesin cellular activities such as spindle separation.

Methods of performing motility assays are well known to those of skill in the art (see, e.g., Hall, et al. (1996), *Biophys. J.*, 71: 3467–3476, Turner et al., 1996, *Anal. Biochem.* 242 (1):20–5; Gittes et al., 1996, *Biophys. J.* 70(1): 418–29; Shirakawa eta/., 1995, J. Exp. Biol. 198: 1809–15; Winkelmann 1995, *Biophys. J.* 68: 2444–53; Winkelmann et al., 1995, *Biophys. J.* 68: 72S, and the like).

In addition to the assays described above, methods known in the art for determining ATPase activity can be used. Preferably, solution based assays are utilized. Alternatively, conventional methods are used. For example, $P_i$ release from kinesin can be quantified. In one preferred embodiment, the ATPase activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 μL of reaction is quenched in 90 μL of cold 0.3 M PCA. Phosphate standards are used so data can be converted to mM inorganic phosphate released. When all reactions and standards have been quenched in PCA, 100 μL of malachite green reagent is added to the to relevant wells in e.g., a microtiter plate. The mixture is developed for 10–15 minutes and the plate is read at an absorbance of 650 nm. If phosphate standards were used, absorbance readings can be converted to mM $P_i$ and plotted over time. Additionally, ATPase assays known in the art include the luciferase assay.

In another preferred method, kinesin activity is measured by the methods disclosed in Ser. No. 09/314,464, filed May 18, 1999, entitled, Compositions and Assay Utilizing ADP or Phosphate for Detecting Protein Modulators.

In a preferred embodiment, the activity of the cellular proliferation protein is increased; in another preferred embodiment, the activity of the cellular proliferation protein is decreased. Thus, bioactive agents that are antagonists are preferred in some embodiments, and bioactive agents that are agonists may be preferred in other embodiments.

In one aspect of the invention, cells containing cellular proliferation sequences are used in drug screening assays by evaluating the effect of drug candidates on cellular proliferation. Cell type include normal cells, and more preferably cells with abnormal proliferative rates including tumor cells, most preferably human tumor cells. Methods of assessing cellular proliferation are known in the art and include growth and viability assays using cultured cells. In such assays, cell populations are monitored for growth and or viability, often over time and comparing samples incubated with various concentrations of the bioactive agent or without the bioactive agent. Cell number can be quantified using agents that such as 3-(4,5-dimethylthiazol-2-yl)-2,5-diphenyltetrazolim bromide (MTT), 3-(4,5-dimethylthiazol-2-yl)-5-(3-carboxymethoxyphenyl)-2-(4-sulfophenyl)-2H-tetrazolium (MTS) [U.S. Pat. No. 5,185,450] and Alamar Blue which are converted to colored or fluorescent compounds in the presence of metabolically active cells. Alternatively, dyes that bind to cellular protein such as sulforhodamine B (SRB) or crystal violet can be used to quantify cell number. Alternatively, cells can be directly counted using a particle counter, such as a Coulter Counter® manufactured by Beckman Coulter, or counted using a microscope to observe cells on a hemocytometer. Preferably, cells counted using the hemocytometer are observed in a solution of trypan blue to distinguish viable from dead cells. Other methods of quantifying cell number are known to those skilled in the art. These assays can be performed on any of the cells, including those in a state of necrosis.

Moreover, apoptosis can be determined by methods known in the art. For example, markers for apoptosis are known, and TUNEL (TdT-mediated dUTP-fluorescein nick end labeling) kits can be bought commercially, for example, Boehringer Mannheim kit, catalog no.168795.

In a preferred embodiment, the methods comprise adding a candidate bioactive agent, as defined above, to a cell comprising cellular proliferation proteins. Preferred cell types include almost any cell. The cells contain a nucleic acid, preferably recombinant, that encodes a cellular proliferation protein. In a preferred embodiment, a library of candidate agents are tested on a plurality of cells.

In one aspect, the assays are evaluated in the presence or absence or previous or subsequent exposure to physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

In one aspect of the invention, the cellular proliferation sequences and cells containing cellular proliferation sequences are used in drug screening assays by evaluating the effect of drug candidates on a "gene expression profile" or expression profile genes. In a preferred embodiment, the expression profiles are used, preferably in conjunction with high throughput screening techniques to allow monitoring for expression profile genes after treatment with a candidate agent. See, Zlokarnik, et al., Science 279, 84–8 (1998).

In one aspect, the expression levels of genes are determined for different cellular states in the cellular proliferation phenotype; that is, the expression levels of genes in normal tissue in proliferating and non-proliferating states, and in abnormal cellular proliferation tissue (and in some cases, for varying severities of cellular proliferation that relate to prognosis, as outlined below) are evaluated to provide expression profiles. Abnormal states include cancer states and other hyper or hypo proliferation states as further defined below.

An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or abnormal cellular proliferation tissue. "Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus abnormal cellular proliferation tissue. That is, genes may be turned on or turned off in a particular state, relative to another state or have a different timing pattern, for example, cancerous cells may have genes which stay on. As is apparent to the skilled artisan, any comparison of two or more states can be made and repeated at various time points. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either unregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology, 14:1675–1680 (1996), hereby expressly incorporated by reference. Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the cellular proliferation protein and standard immunoassays (ELISAs, etc.) or other techniques, including mass spectroscopy assays, 2D gel electrophoresis assays, etc. Thus, the proteins corresponding to cellular proliferation genes, i.e. those identified as being important in a cellular proliferation phenotype, can be evaluated in a cellular proliferation diagnostic test.

In a preferred embodiment nucleic acids encoding the cellular proliferation protein are detected. Although DNA or RNA encoding the cellular proliferation protein may be detected, of particular interest are methods wherein the mRNA encoding a cellular proliferation protein is detected. The presence of mRNA in a sample is an indication that the cellular proliferation gene has been transcribed to form the mRNA, and suggests that the protein is expressed. Probes to detect the mRNA can be any nucleotide/deoxynucleotide probe that is complementary to and base pairs with the mRNA and includes but is not limited to oligonucleotides, cDNA or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a cellular proliferation protein is detected by binding the digoxygenin with an anti-digoxygenin secondary antibody and developed with nitro blue tetrazolium and 5-bromo4-chloro-3-indoyl phosphate.

In one case, having identified a particular gene as up regulated in cellular proliferation, candidate bioactive agents may be screened to modulate this gene's response; preferably to down regulate the gene, although in some circumstances to up regulate the gene. "Modulation" thus includes both an increase and a decrease in gene expression or a change in temporal pattern. The preferred amount of modulation will depend on the original change of the gene expression in normal versus tumor tissue, with changes of at least 10%, preferably 50%, more preferably 100–300%, and in some embodiments 300–1000% or greater. Thus, if a gene exhibits a 4 fold increase in tumor compared to normal tissue, a decrease of about four fold is desired; a 10 fold decrease in tumor compared to normal tissue gives a 10 fold increase in expression for a candidate agent is desired.

In a preferred embodiment, gene expression monitoring is done and a number of genes, i.e. an expression profile, is monitored simultaneously,although multiple protein expression monitoring can be done as well.

In one embodiment, the cellular proliferation nucleic acid probes are attached to biochips as outlined below for the detection and quantification of cellular proliferation sequences in a particular cell.

Generally, in a preferred embodiment, a candidate bioactive agent is added to the cells prior to analysis. Any cell can be used, including normal and abnormal cells, including tumor and non-tumor mammalian, preferably human cells. In some cases, plant cells are used. After the candidate agent has been added and the cells allowed to incubate for some period of time, the sample containing the target sequences to be analyzed is added to the biochip. If required, the target sequence is prepared using known techniques. For example, the sample may be treated to lyse the cells, using known lysis buffers, electroporation, etc., with purification and/or amplification such as PCR occurring as needed, as will be appreciated by those in the art. For example, an in vitro transcription with labels covalently attached to the nucleosides is done. Generally, the nucleic acids are labeled with biotin-FITC or PE, or with cy3 or cy5.

In a preferred embodiment, the target sequence is labeled with, for example, a fluorescent, a chemiluminescent, a chemical, or a radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,1.17, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Once the assay is run, the data is analyzed to determine the expression levels, and changes in expression levels as between states, of individual genes, forming a gene expression profile.

In one aspect, the screens are done to identify drugs or bioactive agents that modulate the cellular proliferation phenotype. Specifically, there are several types of screens that can be run. A preferred embodiment is in the screening of candidate agents that can induce or suppress a particular expression profile, thus preferably generating the associated phenotype. That is, candidate agents that can mimic or produce an expression profile in cellular proliferation similar to the expression profile of normal non-cancerous tissue is expected to result in a suppression of the cellular proliferation phenotype. Thus, in this embodiment, mimicking an expression profile, or changing one profile to another, is the goal.

In a preferred embodiment, as for the diagnosis and prognosis applications discussed below, having identified the differentially expressed genes important in any one state as further described below, screens can be run to alter the expression of the genes individually. That is, screening for modulation of regulation of expression of a single gene can be done; that is, rather than try to mimic all or part of an expression profile, screening for regulation of individual genes can be done. Thus, for example, particularly in the case of target genes whose presence, absence or temporal pattern is unique between two states, screening is done for modulators of the target gene expression. In a preferred embodiment, the target gene encodes the cellular proliferation protein described herein. Thus, screening of candidate agents that modulate the cellular proliferation phenotype either at the gene expression level or the protein level can be done.

In addition screens can be done for novel genes that are induced in response to a candidate agent. After identifying a candidate agent based upon its ability to suppress a cellular proliferation expression pattern leading to a normal expression pattern, or modulate a single cellular proliferation gene expression profile so as to mimic the expression of the gene from normal tissue, a screen as described above can be performed to identify genes that are specifically modulated in response to the agent. Comparing expression profiles between normal tissue and agent treated cellular proliferation tissue reveals genes that are not expressed in normal tissue or cellular proliferation tissue, but are expressed in agent treated tissue. These agent specific sequences can be identified and used by any of the methods described herein for cellular proliferation genes or proteins. In particular these sequences and the proteins they encode find use in marking or identifying agent treated cells. In addition, antibodies can be raised against the agent induced proteins and used to target novel therapeutics to the treated cellular proliferation tissue sample.

In one embodiment, a candidate agent is administered to a population of cellular proliferation cells, that thus has an associated cellular proliferation expression profile. By "administration" or "contacting"herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e. a peptide) may be put into a viral construct such as a retroviral construct and added to the cell, such that expression of the peptide agent is accomplished; see PCT US97/01019, hereby expressly incorporated by reference. The phrase "under conditions which allow the cell to uptake the candidate agent" means that the cell is biologically involved in the uptake and intracellular action, or by action at the cell surface in that the agent is not injected into the cell. It is understood that targeting ligands and biochemically agents can be used to facilitate the uptake, however, this differs from mechanical injection. Mechanical injection is explicitly excluded from the definition of "taken up by the cell" as used herein, and is excluded from conditions inducive to high throughput assays as used herein.

Once the candidate agent has been administered to the cells, the cells can be washed if desired and are allowed to incubate under preferably physiological conditions for some period of time. The cells are then harvested and a new gene expression profile is generated, as outlined herein.

Thus, for example, cellular proliferation tissue may be screened for agents that reduce or suppress the cellular proliferation phenotype. A change in at least one gene of the expression profile indicates that the agent has an effect on cellular proliferation activity. By defining such a signature for the cellular proliferation phenotype, screens for new drugs that alter the phenotype can be devised. With this approach, the drug target need not be known and need not be represented in the original expression screening platform, nor does the level of transcript for the target protein need to change.

In all the methods provided herein, bioactive agents are identified. Similarly, compounds which interfere with binding or interaction between the cellular proliferation protein and an identified binding or modulating agent can be identified. Moreover, transgenic models as discussed below may be used to identify bioactive agents. Compounds with pharmacological activity are able to enhance or interfere with the activity of the cellular proliferation protein. The compounds can be used in further assays so as to confirm activity wherein necessary or optimize conditions including varying the identified molecules. In a preferred embodiment, the agents are used as therapeutics as discussed below.

In a further aspect of the present invention, methods of modulating cellular proliferation in cells or organisms are provided. In one embodiment, the methods comprise administering to a cell an anti-cellular proliferation antibody as further discussed below that reduces or eliminates the biological activity of an endogeneous cellular proliferation protein. In a preferred embodiment, a nucleic acid encoding said antibody is administered. Agents identified to modulate cellular proliferation can also be used. Alternatively, the methods comprise administering to a cell or organism a composition comprising a cellular proliferation sequence.

In a preferred embodiment, for example when the cellular proliferation sequence is down-regulated in cellular proliferation, the activity of the cellular proliferation gene is increased by increasing the amount of cellular proliferation in the cell, for example by overexpressing the endogeneous cellular proliferation or by administering a gene encoding the cellular proliferation sequence, using known gene-therapy techniques, for example. In a preferred embodiment, the gene therapy techniques include the incorporation of the exogeneous gene using enhanced homologous recombination (EHR), for example as described in PCT/US93/03868, hereby incorporated by reference in its entirety. Alternatively, for example when the cellular proliferation sequence is up-regulated in cellular proliferation, the activity of the endogeneous cellular proliferation gene is decreased, for example by the administration of a cellular proliferation antisense nucleic acid. Preferably, as discussed below, cellular proliferation is inhibited.

Thus, In one embodiment, a method of inhibiting cell division is provided. In a preferred embodiment, a method of inhibiting tumor growth is provided. In a further embodiment, methods of treating cells or individuals with cancer are provided. The method comprises administration of a cellular proliferation inhibitor.

In one embodiment, a cellular proliferation inhibitor is an antibody as discussed above and further described below. In another embodiment, the cellular proliferation inhibitor is an antisense molecule as discussed above. Antisense molecules as used herein include antisense or sense oligonucleotides comprising a singe-stranded nucleic acid sequence (either RNA or DNA) capable of binding to target mRNA (sense) or DNA (antisense) sequences for cellular proliferation molecules. A preferred antisense molecule is for KSP or for a ligand or activator thereof. Antisense or sense oligonucleotides, according to the present invention, comprise a fragment generally at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Antisense molecules may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment. Moreover, knock out models can include knocking out expression, rather than the genome, such as by the use ribozymes. In one case, ribozymes are a preferred KSP inhibitor.

As discussed above, the methods and compositions herein are not limited to cancer. Disease states which can be treated by the methods and compositions provided herein include, but are not limited to, cancer (further discussed below), restenosis, autoimmune disease, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals afflicted or impending affliction with any one of these disorders or states.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastom, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (rheningioma, meningiosarcoma, gliomatosis), brain (astrocytoma, medulloblastoma, glioma, ependymoma, germinoma [pinealoma, glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematoloaic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. The cancer can be solid tumors or metastatic. Thus, the term "cancerous cell" as provided herein, includes a cell afflicted by any one of the above identified conditions.

In another aspect herein, diagnostic assays are provided herein. In one embodiment, the cellular proliferation sequences are used in the diagnostic assays. This can be done on an individual gene or corresponding polypeptide level. In a preferred embodiment, the expression profiles are used, preferably in conjunction with high throughput screening techniques to allow monitoring for expression profile genes and/or corresponding polypeptides. In a preferred embodiment, in situ hybridization of labeled cellular proliferation nucleic acid probes to tissue arrays is done. For example, arrays of tissue samples, including cellular proliferation tissue in various states and or time points and/or normal tissue, are made. In situ hybridization as is known in the art can then be done. It is understood that conventional antibody and protein localization methods can also be used in diagnostic assays herein.

It is understood that when comparing the fingerprints between an individual and a standard, the skilled artisan can make a diagnosis as well as a prognosis. It is further understood that the genes which indicate the diagnosis may differ from those which indicate the prognosis.

In a preferred embodiment, the cellular proliferation sequences are used in prognosis assays. As above, gene expression profiles can be generated that correlate to cellular proliferation severity, in terms of long term prognosis. Again, this may be done on either a protein or gene level, with the use of genes being preferred. In both the diagnostic and prognostic assays, the cellular proliferation probes can be attached to biochips as described below for the detection and quantification of cellular proliferation sequences in a tissue or patient.

Accordingly, disorders based on mutant or variant cellular proliferation genes may also be determined. In one embodiment, the invention provides methods for identifying cells containing variant cellular proliferation genes comprising determining all or part of the sequence of at least one endogenous cellular proliferation genes in a cell. As will be appreciated by those in the art, this may be done using any number of sequencing techniques. In a preferred embodiment, the invention provides methods of identifying the cellular proliferation genotype of an individual comprising determining all or part of the sequence of at least one cellular proliferation gene of the individual. This is generally done in at least one tissue of the individual, and may include the evaluation of a number of tissues or different samples of the same tissue. The method may include comparing the sequence of the sequenced cellular proliferation gene to a known cellular proliferation gene, i.e. a wild-type gene.

The sequence of all or part of the cellular proliferation gene can then be compared to the sequence of a known cellular proliferation gene to determine if any differences exist. This can be done using any number of known homology programs, such as Bestfit, etc. In a preferred embodiment, the presence of a difference in the sequence between the cellular proliferation gene of the patient and the known cellular proliferation gene is indicative of a disease state or a propensity for a disease state, as outlined herein.

In a preferred embodiment, the cellular proliferation genes are used as probes to determine the number of copies of the cellular proliferation gene in the genome.

In another preferred embodiment cellular proliferation genes are used as probes to determine the chromosomal localization of the cellular proliferation genes. Information such as chromosomal localization finds use in providing a diagnosis or prognosis in particular when chromosomal abnormalities such as translocations, and the like are identified in cellular proliferation gene loci.

Once a determination has been made regarding the proliferation state of a cell, if desired, the compositions or agents described herein can be administered. The compounds having the desired pharmacological activity may be administered in a physiologically acceptable carrier (also called a pharmaceutically acceptable carrier) to a host. Depending upon the manner of introduction, the compounds may be formulated in a variety of ways as discussed below. The concentration of therapeutically active compound in the formulation may vary from about 0.1–100 wt. %. The agents may be administered alone or in combination with other treatments, e.g., radiation.

Thus, in a preferred embodiment, cellular proliferation proteins and modulators are administered as therapeutic agents. Similarly, cellular proliferation genes (including both the full-length sequence, partial sequences, or regulatory sequences of the cellular proliferation coding regions) can be administered in gene therapy applications, as is known in the art. These cellular proliferation genes can include antisense applications, either as gene therapy (i.e. for incorporation into the genome) or as antisense compositions, as will be appreciated by those in the art.

In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The administration of the cellular proliferation proteins and modulators of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the cellular proliferation proteins and modulators may be directly applied as a solution or spray.

In one embodiment, a therapeutically effective dose of a cellular proliferation protein or modulator thereof is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for cellular proliferation degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

In a preferred embodiment, cellular proliferation genes are administered as DNA vaccines, either single genes or combinations of cellular proliferation genes. Naked DNA vaccines are generally known in the art. Brower, Nature Biotechnology, 16:1304–1305 (1998).

In one embodiment, cellular proliferation genes of the present invention are used as DNA vaccines. Methods for the use of genes as DNA vaccines are well known to one of ordinary skill in the art, and include placing a cellular proliferation gene or portion of a cellular proliferation gene under the control of a promoter for expression in a cellular proliferation patient. The cellular proliferation gene used for DNA vaccines can encode full-length cellular proliferation proteins, but more preferably encodes portions of the cellular proliferation proteins including peptides derived from the cellular proliferation protein. In a preferred embodiment a patient is immunized with a DNA vaccine comprising a plurality of nucleotide sequences derived from a cellular proliferation gene. Similarly, it is possible to immunize a patient with a plurality of cellular proliferation genes or portions thereof as defined herein. Without being bound by theory, expression of the polypeptide encoded by the DNA vaccine, cytotoxic T-cells, helper T-cells and antibodies are induced which recognize and destroy or eliminate cells expressing cellular proliferation proteins.

In a preferred embodiment, the DNA vaccines include a gene encoding an adjuvant molecule with the DNA vaccine. Such adjuvant molecules include cytokines that increase the immunogenic response to the cellular proliferation polypeptide encoded by the DNA vaccine. Additional or alternative adjuvants are known to those of ordinary skill in the art and find use in the invention.

In another preferred embodiment cellular proliferation genes find use in generating animal models of cellular proliferation. As is appreciated by one of ordinary skill in the art, when the cellular proliferation gene identified is repressed or diminished in cellular proliferation tissue, gene therapy technology wherein antisense RNA directed to the cellular proliferation gene will also diminish or repress expression of the gene. An animal generated as such serves as an animal model of cellular proliferation that finds use in screening bioactive drug candidates. Similarly, gene knockout technology, for example as a result of homologous recombination with an appropriate gene targeting vector, will result in the absence of the cellular proliferation protein. When desired, tissue-specific expression or knockout of the cellular proliferation protein may be necessary.

It is also possible that the cellular proliferation protein is overexpressed in cellular proliferation. As such, transgenic animals can be generated that overexpress the cellular proliferation protein. Depending on the desired expression level, promoters of various strengths can be employed to express the transgene. Also, the number of copies of the integrated transgene can be determined and compared for a determination of the expression level of the transgene. Animals generated by such methods find use as animal models of cellular proliferation and are additionally useful in screening for bioactive molecules to treat cellular proliferation.

In a preferred embodiment, biochips are provided herein. Nucleic acid probes to cellular proliferation nucleic acids (both the nucleic acid sequences outlined in the figures and/or the complements thereof are made. The nucleic acid probes attached to the biochip are designed to be substantially complementary to the cellular proliferation nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (i.e. have some sequence in common), or separate.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably fluoresce. A preferred substrate is described in copending application entitled Reusable Low Fluorescent Plastic Biochip filed Mar. 15, 1999, herein incorporated by reference in its entirety.

Generally the substrate is planar, although as will be appreciated by those in the art, other configurations of substrates may be used as well. For example, the probes may be placed on the inside surface of a tube, for flow-through sample analysis to minimize sample volume. Similarly, the substrate may be flexible, such as a flexible foam, including closed cell foams made of particular plastics.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix GeneChip™ technology.

In another preferred embodiment anti-cellular proliferation antibodies are provided. In one case, the cellular proliferation protein is to be used to generate antibodies, for example for immunotherapy. Wherein a fragment of the cellular proliferation protein is used, the cellular proliferation protein should share at least one epitope or determinant with the full length protein. By "epitope" or "determinant" herein is meant a portion of a protein which will generate and/or bind an antibody or T-cell receptor in the context of MHC. Thus, in most instances, antibodies made to a smaller cellular proliferation protein will be able to bind to the full length protein. In a preferred embodiment, the epitope is unique; that is, antibodies generated to a unique epitope show little or no cross-reactivity.

In one embodiment, the term "antibody" includes antibody fragments, as are known in the art, including Fab, $Fab_2$, single chain antibodies (Fv for example), chimeric antibodies, etc., either produced by the modification of whole antibodies or those synthesized de novo using recombinant DNA technologies.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the KSP or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include the KSP polypeptide or fragment thereof or a fusion protein thereof. Generally, either peripheral blood lymphocytes ("PBLs") are used. if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. [*Goding, Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens. In the present case, one of the binding specificities is for the KSP or a fragment thereof, the other one is for any other antigen, and preferably for a cell-surface protein or receptor or receptor subunit, preferably one that is tumor specific.

In a preferred embodiment, the antibodies to cellular proliferation are capable of reducing or eliminating the biological function of cellular proliferation, as is described below. That is, the addition of anti-KSP antibodies (either polyclonal or preferably monoclonal) to cellular proliferation (or cells containing cellular proliferation) may reduce or eliminate the cellular proliferation activity. Generally, at least a 25% decrease in activity is preferred, with at least about 50% being particularly preferred and about a 95–100% decrease being especially preferred.

In a preferred embodiment the antibodies to the cellular proliferation proteins are humanized antibodies. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991);

Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is A described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

By immunotherapy is meant treatment of cellular proliferation with an antibody raised against cellular proliferation proteins. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen.

As will be appreciated by one of ordinary skill in the art, the antibody may be a competitive, non-competitive or uncompetitive inhibitor of protein binding to the cellular proliferation protein. Preferably, the antibody is also an antagonist of the cellular proliferation protein. In one aspect, when the antibody prevents the binding of other molecules to the cellular proliferation protein, the antibody prevents growth of the cell. The antibody also sensitizes the cell to cytotoxic agents, including, but not limited to TNF-α, TNF-β, IL-1, INF-γ and IL-2, or chemotherapeutic agents including 5FU, vinblastine, actinomycin D, cisplatin, methotrexate, and the like.

In another preferred embodiment, the antibody is conjugated to a therapeutic moiety. In one aspect the therapeutic moiety is a small molecule that modulates the activity of the cellular proliferation protein. In another aspect the therapeutic moiety modulates the activity of molecules associated with or in close proximity to the cellular proliferation protein.

In a preferred embodiment, the therapeutic moiety may also be a cytotoxic agent. In this method, targeting the cytotoxic agent to tumor tissue or cells, results in a reduction in the number of afflicted cells, thereby reducing symptoms associated with cellular proliferation. Cytotoxic agents are numerous and varied and include, but are not limited to, cytotoxic drugs or toxins or active fragments of such toxins. Suitable toxins and their corresponding fragments include diptheria a chain, exotoxin a chain, ricin a chain, abrin a chain, curcin, crotin, phenomycin, enomycin and the like. Cytotoxic agents also include radiochemicals made by conjugating radioisotopes to antibodies raised against cellular proliferation proteins, or binding of a radionuclide to a chelating agent that has been covalently attached to the antibody. Targeting the therapeutic moiety to cellular proliferation proteins not only serves to increase the local concentration of therapeutic moiety in the cellular proliferation afflicted area, but also serves to reduce deleterious side effects that may be associated with the therapeutic moiety.

Preferably, the antibody is conjugated to a protein which facilitates entry into the cell. In one case, the antibody enters the cell by endocytosis. In another embodiment, a nucleic acid encoding the antibody is administered to the individual or cell. The nucleic acid is identified based on the sequence of the antibody, determined by standard recombinant techniques. Moreover, wherein the cellular proliferation protein can be targeted within a cell, i.e., the nucleus, an antibody thereto contains a signal for that target localization, i.e., a nuclear localization signal.

In a preferred embodiment, the cellular proliferation antibodies of the invention specifically bind to cellular proliferation proteins. By "specifically bind" herein is meant that the antibodies bind to the protein with a binding constant in the range of at least $10^{4}$–$10^{6}$ M$^{-1}$, with a preferred range being $10^{-7}$–$10^{-9}$ M$^{-1}$.

It is understood that the examples described above in no way serve to limit the true scope of this invention, but rather are presented for illustrative purposes. All references cited herein are incorporated by reference in their entirety as well as the sequences cited therein or having a GenBank accession number.

We claim:

1. An isolated microtubule motor protein, wherein the protein has greater than 98% amino acid sequence identity to SEQ ID NO:4 as measured using a WU-BLAST-2 sequence comparison algorithm with the following adjustable parameters; overlap span of 1, overlap fraction of 0.125, and word threshold of 11 and with the other parameters set to default values and wherein the protein binds microtubules and has ATPase activity.

2. An isolated protein having an amino acid sequence of SEQ ID NO:4, SEQ ID NO:6, SEQ ID NO:8, or SEQ ID NO:10.

3. An isolated protein of claim 2 having an amino acid sequence of SEQ ID NO:4.

4. An isolated protein of claim 2 having an amino acid sequence of SEQ ID NO:6.

5. An isolated protein of claim 2 having an amino acid sequence of SEQ ID NO:8.

6. An isolated protein of claim 2 having an amino acid sequence of SEQ ID NO:10.

7. An isolated microtubule motor protein, wherein the protein has greater than 98% amino acid sequence identity to SEQ ID NO:4 as measured using a PILEUP sequence comparison algorithm with the following parameters: default gap weight of 3.00, a default gap length weight of 0.10, and weighted end gaps and wherein the protein binds microtubules and has ATPase activity.

* * * * *

SEQUENCE LISTING

<160> NUMBER OF SEQ ID NOS: 10

<210> SEQ ID NO 1
<211> LENGTH: 3740
<212> TYPE: DNA
<213> ORGANISM: Human

<400> SEQUENCE: 1

```
gaattccgtc gaacatccag ccattcaata ggctgacaag acagattgat taattgcact      60
tgaaaggtca acgtaccctt agtgtctctg tgtttctgag aggtttagaa ggcagcaaaa     120
agttttctct aatcggaaag tgttgataag ggtcattact tagaatcctc tcctgcatct     180
gaacatattg gtatacggag agtgtatatt gcagattgta agagttgttt aacacaagaa     240
```

-continued

```
agaagaatat caagatgatt ggatcgtaag cctgaatagt ggccatgcta attagatacc      300
tactcatgtt taaaactgta aatgatttta tttcaagact tggctttctc cttggttgag      360
gacccattcc ggaggaaaag gaaatctaag tgatggcttc atctgtgaaa acagagatgt      420
cttaaatgaa ggcttcaagt gcataacatt agaacttaat tctgaaactg aacactggta      480
tgagctgtta ggatgtagaa tgtagatgct atcacatgga agaaactaca ttaattcact      540
aaccccagaa gtggctctag caggagtttg gccgggcgtg tcacttgaac gggcaacaga      600
gtaaattcag tattaaattg aagtagttct tggcgtcgcg tggtggtgag tagaatgtga      660
gctcaaggag tttaccgaaa tctttgcgtc ctaatgaagc atcaaatttt tggagatcta      720
gactacagag aaattacaga ggacaactgg ttacaatact tgaacttgga gagctcgggg      780
cccttgtagc aggattctcc tcaatcttga ataagcctgg atagaaact ctgaagaaag      840 aattgattga tggataatac ttgaaaccaa tcacatcaga acacagttga aggcagttgc      900
tgtttaatag aagtacataa ttactacagt ctcagatttc tacaggaatt ccccaactgt      960
cattgacaga gtatactgtt cacaaaagcc aggaactttt gtgaaaatag atatagtcat     1020
cacaggaacc actctgatag aatctctgaa gggaacaggt cagacatcat ttcttgatcg     1080
aaaccataag atatcccaaa gaactgaaca tgatgctaag aggcagttcg gtgtggatta     1140
aagacaaagg agcacttggt gggggttggc ttgagccttc tgtaatccca gaccagcctg     1200
tgggcacacc cagaagcggg caagactcgt gaattttggg gttcattttt ttaggaatta     1260
gccaaattcg atgcagacca tcctgtacga acatacacg tgttgtttga tggccaaaca      1320
gtatacctgt tgagaaacta taatgaagat gtttgatgat acaagaacac agctactcta     1380
tatgaaagat tgatcttgca agctggaaaa agaacacct tggagggcga ggaaactcta      1440
agtgaatcag tttaaaacga ttttagagta aaaaattgga aaatgaactc tcaaaaacac     1500
tttggaaaga agaaactaca ccaacacaaa tatggaagaa gaccttatt agcacttggt      1560 taatatgatt gattaatgtt ggtgtctatt ggccgataag taacaatcta atgtggaaag     1620
caagttaatt acagaaacca caaaatgact cagaaattta actcaatgga cacaagaaca     1680
acttcacaac tgagaaatga gatgactata aattggtttc aggtacgacc acgtgaacaa     1740
ctgttcagat ggggcagtag ttcatcaata aaacagaggt tacaaagagc aattttattg     1800
tgtatagata gctaactttg gccaacgtgt cctgtaatcg gttgcagtgg tctcaaaaaa     1860
tatctacccg ggatttgcac gtctgcgaag atttaatttg aaagaagtt ttttgatatg      1920 tccaattctg tggcactgga ggaagaggat tactgataat gcttttttgat tccccgtaac    1980 ggatgaagtc gatgaatgca aactacgatt aggaagtgaa tataaatcaa tcatgttcct    2040
tacaagaaca gagtacattg gaaactcacc agatcttgct catgagtgga tgctgttgag   2100
tgaccagtgt tttgcaagaa tactgaggag aaaagatgta tgcagaagct attaattaag   2160
tggtaatgtg atctctcaca actaaagaa actcaagact actgaaaatc gatagaagat     2220
acatgaacta cctaactgaa gaatctttgg acttagtagt ttttcacagt taaccaagaa    2280
caacctggaa agtttatttt cttattggag agatggacgt tgatgaagat gactaagctt    2340
accacagagg tctccttgat aaacaacaaa tactgaagaa tggcgggtt cattaacaca     2400 cagattacct tttaaagaaa ttaaaagaa ggaggctgag cgctaaaacc ccagctactg      2460
agccaaaggt taaatttaa attttctgt atgtaaatac aagaaagagg gcagagcgga     2520
agtgtacgaa gtgtttggag gatgaagtta aaaacttta cccttggctg ggtactgaat      2580
```

-continued

```
cttcttaatc aagagaggag tatcaaattt tactctagtc gatggagaag aacattggcc    2640
tccctgttga tatcgagaat tctataattg gaatatgctc aaaaaagctc gcagcccgtg    2700
aaattaactg gaggagctga aaatctgacc actaaattac aaacttcatg tctggtctcc    2760
caggatattt gatggcagct ctgtcttcca tctattccag caatcattag gatcttctaa    2820
aatagtcaac caaaaaaaaa caagaaaata gacctgaaga acagagagat gtccaggaaa    2880
caaaaatttt ggtacaaaat aaaatatctc tctgaacagt gttgtaagcc aaggcagctc    2940
aaattgatag aattgctttc aaaagttatt cagctgaaaa aagagacaa cctctaagtc    3000 ccattttttcc ctggagaggt ctgcgagccc aacttaaaaa tatatatatc gcgggtggat    3060
ttcgtctctg gggaggctga acaccactac aaaagatata catccctata gtatttctag    3120
agaaggggaa aagctagcgc ctggaggatt catctactaa ttatgggcta caatggaagg    3180
gtataattcc tttcagtcaa catcatctga tgataattaa tagaaaaggg gttcccactc    3240
agcttgttaa gttctggagc ctttgggaag ctaaactaac caacaatttc atagagcaaa    3300
ttattaagga agaaaaatgg ttcaagaaga atagggttac tgcaaaataa aacttgttaa    3360
atgctgccag attccaaact ttggcaaaaa caaagcaaaa gtgtctctgc aaaatgtgtc    3420
cagcagaaag gttcactgga taaagcatat ggaactcaga ccatttgttc caataaagca    3480
tctgtgcttt atatacagca gtgctgattc tggttgaaga aagagactga gggtatcttc    3540
aatgttgtga atgagaaaca cacaaaatct tggaacagga tatacccatc ggaaacagcc    3600
ttccggatgt aagagccatc agcataaaaa ctaaagtgga agatcaacct taaaacctga    3660
agccgggcgc tgcttgagcc ttaaaaatta ggcacgagaa actccagcct aggcagtact    3720
gttcactttg ttttcatata                                                3740
```

<210> SEQ ID NO 2
<211> LENGTH: 1053
<212> TYPE: PRT
<213> ORGANISM: Human

<400> SEQUENCE: 2

```
Met Ala Ser Gln Pro Asn Ser Ala Lys Lys Lys Glu Glu Lys Gly
  1               5                  10                  15

Lys Asn Ile Gln Val Val Arg Cys Arg Pro Phe Asn Leu Ala Glu
                 20                  25                  30

Arg Lys Ala Ser Ala His Ser Ile Val Glu Cys Asp Pro Val Arg Lys
         35                  40                  45

Glu Val Ser Val Arg Thr Gly Gly Leu Ala Asp Lys Ser Ser Arg Lys
 50                  55                  60

Thr Tyr Thr Phe Asp Met Val Phe Gly Ala Ser Thr Lys Gln Ile Asp
 65                  70                  75                  80

Val Tyr Arg Ser Val Val Cys Pro Ile Leu Asp Glu Val Ile Met Gly
                 85                  90                  95

Tyr Asn Cys Thr Ile Phe Ala Tyr Gly Gln Thr Gly Thr Gly Lys Thr
                100                 105                 110

Phe Thr Met Glu Gly Glu Arg Ser Pro Asn Glu Glu Tyr Thr Trp Glu
        115                 120                 125

Glu Asp Pro Leu Ala Gly Ile Ile Pro Arg Thr Leu His Gln Ile Phe
    130                 135                 140

Glu Lys Leu Thr Asp Asn Gly Thr Glu Phe Ser Val Lys Val Ser Leu
145                 150                 155                 160

Leu Glu Ile Tyr Asn Glu Glu Leu Phe Asp Leu Leu Asn Pro Ser Ser
```

-continued

```
                    165                 170                 175
Asp Val Ser Glu Arg Leu Gln Met Phe Asp Asp Pro Arg Asn Lys Arg
                180                 185                 190
Gly Val Ile Ile Lys Gly Leu Glu Glu Ile Thr Val His Asn Lys Asp
            195                 200                 205
Glu Val Tyr Gln Ile Leu Glu Lys Gly Ala Ala Lys Arg Thr Thr Ala
        210                 215                 220
Ala Thr Leu Met Asn Ala Tyr Ser Ser Arg Ser His Ser Val Phe Ser
225                 230                 235                 240
Val Thr Ile His Met Lys Glu Thr Thr Ile Asp Gly Glu Glu Leu Val
                245                 250                 255
Lys Ile Gly Lys Leu Asn Leu Val Asp Leu Ala Gly Ser Glu Asn Ile
            260                 265                 270
Gly Arg Ser Gly Ala Val Asp Lys Arg Ala Arg Glu Ala Gly Asn Ile
        275                 280                 285
Asn Gln Ser Leu Leu Thr Leu Gly Arg Val Ile Thr Ala Leu Val Glu
    290                 295                 300
Arg Thr Pro His Val Pro Tyr Arg Glu Ser Lys Leu Thr Arg Ile Leu
305                 310                 315                 320
Asp Ser Leu Gly Gly Arg Thr Arg Thr Ser Ile Ile Ala Thr Ile Ser
                325                 330                 335
Pro Ala Ser Leu Asn Leu Glu Glu Thr Leu Ser Thr Leu Glu Tyr Ala
            340                 345                 350
His Arg Ala Lys Asn Ile Leu Asn Lys Pro Glu Val Asn Gln Lys Leu
        355                 360                 365
Thr Lys Lys Ala Leu Ile Lys Glu Tyr Thr Glu Ile Glu Arg Leu
    370                 375                 380
Lys Arg Asp Leu Ala Ala Ala Arg Glu Lys Asn Gly Val Tyr Ile Ser
385                 390                 395                 400
Glu Glu Asn Phe Arg Val Met Ser Gly Lys Leu Thr Val Gln Glu Glu
                405                 410                 415
Gln Ile Val Glu Leu Ile Glu Lys Ile Gly Ala Val Glu Glu Glu Leu
            420                 425                 430
Asn Arg Val Thr Ala Leu Phe Met Asp Asn Lys Asn Glu Leu Asp Gln
        435                 440                 445
Cys Lys Ser Asp Leu Gln Asn Lys Thr Gln Glu Leu Glu Thr Thr Gln
    450                 455                 460
Lys His Leu Gln Glu Thr Lys Leu Gln Leu Val Lys Glu Glu Tyr Ile
465                 470                 475                 480
Thr Ser Ala Leu Glu Ser Thr Glu Glu Lys Leu His Asp Ala Ala Ser
                485                 490                 495
Lys Leu Leu Asn Thr Val Glu Glu Thr Thr Lys Asp Val Ser Gly Leu
            500                 505                 510
His Ser Lys Leu Asp Arg Ala Lys Lys Ala Val Asp Gln His Asn Ala
        515                 520                 525
Glu Ala Gln Asp Asp Ile Phe Gly Lys Asn Leu Ser Leu Phe Asn Asn
    530                 535                 540
Met Glu Glu Leu Ile Lys Asp Gly Ser Lys Lys Ala Met Leu Glu Val
545                 550                 555                 560
His Lys Thr Leu Phe Gly Asn Leu Leu Ser Ser Val Ser Ala Leu
                565                 570                 575
Asp Thr Ile Thr Thr Val Ala Leu Gly Ser Leu Thr Ser Ile Pro Glu
            580                 585                 590
```

```
Asn Val Ser Thr His Val Ser Gln Ile Phe Asn Met Ile Leu Lys Glu
            595                 600                 605
Gln Ser Leu Ala Ala Glu Ser Lys Thr Val Leu Gln Glu Leu Ile Asn
            610                 615                 620
Val Leu Lys Thr Asp Leu Leu Ser Ser Leu Glu Met Ile Leu Ser Pro
625                 630                 635                 640
Thr Val Val Ser Ile Leu Lys Ile Asn Ser Gln Leu Lys His Ile Phe
                645                 650                 655
Lys Thr Ser Leu Thr Val Ala Asp Lys Ile Glu Asp Gln Lys Lys Arg
            660                 665                 670
Asn Ser Asp Gly Phe Leu Ser Ile Leu Cys Asn Asn Leu Glu His Glu
            675                 680                 685
Leu Gln Glu Asn Thr Ile Cys Ser Leu Val Glu Ser Gln Lys Gln Cys
            690                 695                 700
Gly Asn Leu Thr Glu Asp Leu Lys Thr Ile Lys Gln Thr His Ser Gln
705                 710                 715                 720
Glu Leu Cys Lys Leu Met Asn Trp Thr Glu Arg Phe Cys Ala Leu Glu
                725                 730                 735
Glu Lys Cys Glu Asn Ile Gln Lys Pro Leu Ser Ser Val Gln Glu Asn
            740                 745                 750
Ile Gln Gln Lys Ser Lys Asp Ile Val Asn Lys Met Thr Phe His Ser
            755                 760                 765
Gln Lys Phe Cys Ala Asp Ser Asp Gly Phe Ser Gln Glu Leu Arg Asn
            770                 775                 780
Phe Asn Gln Glu Gly Thr Lys Leu Val Glu Glu Ser Val Lys His Ser
785                 790                 795                 800
Asp Lys Leu Asn Gly Asn Leu Glu Lys Ile Ser Gln Ile Thr Glu Arg
                805                 810                 815
Cys Glu Ser Leu Asn Thr Arg Thr Val Tyr Phe Ser Glu Gln Trp Val
            820                 825                 830
Ser Ser Leu Asn Glu Arg Glu Glu Leu His Asn Leu Leu Glu Val Val
            835                 840                 845
Ser Gln Cys Cys Glu Ala Ser Ser Ser Asp Ile Thr Glu Lys Ser Asp
            850                 855                 860
Gly Arg Lys Ala Ala His Glu Lys Gln His Asn Ile Phe Leu Asp Gln
865                 870                 875                 880
Met Thr Ile Asp Glu Asp Lys Leu Ile Ala Gln Asn Leu Glu Leu Asn
                885                 890                 895
Glu Thr Ile Lys Ile Gly Leu Thr Lys Leu Asn Cys Phe Leu Glu Gln
            900                 905                 910
Asp Leu Lys Leu Asp Ile Pro Thr Gly Thr Thr Pro Gln Arg Lys Ser
            915                 920                 925
Tyr Leu Tyr Pro Ser Thr Leu Val Arg Thr Glu Pro Arg Glu His Leu
            930                 935                 940
Leu Asp Gln Leu Lys Arg Lys Gln Pro Glu Leu Leu Met Met Leu Asn
945                 950                 955                 960
Cys Ser Glu Asn Asn Lys Glu Glu Thr Ile Pro Asp Val Asp Val Glu
                965                 970                 975
Glu Ala Val Leu Gly Gln Tyr Thr Glu Glu Pro Leu Ser Gln Glu Pro
            980                 985                 990
Ser Val Asp Ala Gly Val Asp Cys Ser Ser Ile Gly Gly Val Pro Phe
            995                 1000                1005
```

-continued

Phe Gln His Lys Lys Ser His Gly Lys Asp Lys Glu Asn Arg Gly Ile
    1010                1015                1020

Asn Thr Leu Glu Arg Ser Lys Val Glu Thr Thr Glu His Leu Val
1025                1030                1035                1040

Thr Lys Ser Arg Leu Pro Leu Arg Ala Gln Ile Asn Leu
                1045                1050

<210> SEQ ID NO 3
<211> LENGTH: 1149
<212> TYPE: DNA
<213> ORGANISM: Human

<400> SEQUENCE: 3

| | | | | | |
|---|---|---|---|---|---|
| atggcgtgcc | agccaaattc | gtctgcgaag | aagaaagagg | agaagggggaa | gaacatccag | 60 |
| gtggtggtga | gatgcagacc | atttaatttg | gcagagcgga | aagctagcgc | ccattcaata | 120 |
| gtagaatgtg | atcctgtacg | aaaagaagtt | agtgtacgaa | ctggaggatt | ggctgacaag | 180 |
| agctcaagga | aaacatacac | ttttgatatg | gtgtttggag | catctactaa | acagattgat | 240 |
| gtttaccgag | tgttgtttg | tccaattctg | atgaagtta | ttatgggcta | taattgcact | 300 |
| atctttgcgt | atggccaaac | tggcactgga | aaaactttta | caatggaagg | tgaaaggtca | 360 |
| cctaatgaag | agtatacctg | ggaagaggat | cccttggctg | gtataattcc | acgtaccctt | 420 |
| catcaaattt | ttgagaaact | tactgataat | ggtactgaat | tttcagtcaa | agtgtctctg | 480 |
| ttggagatct | ataatgaaga | gcttttgat | cttcttaatc | catcatctga | tgtttctgag | 540 |
| agactacaga | tgtttgatga | tccccgtaac | aagagaggag | tgataattaa | aggtttagaa | 600 |
| gaaattacag | tacacaacaa | ggatgaagtg | tatcaaattt | tagaaaaggg | ggcagcaaaa | 660 |
| aggacaactg | cagctactct | gatgaatgca | tactctagtc | gttcccactc | agttttctct | 720 |
| gttacaatac | atatgaaaga | aactacgatt | gatggagaag | agcttgttaa | aatcggaaag | 780 |
| ttgaacttgg | ttgatcttgc | aggaagtgaa | aacattggcc | gttctggagc | tgttgataag | 840 |
| agagctcggg | aagctggaaa | tataaatcaa | tccctgttga | cttgggaag | ggtcattact | 900 |
| gcccttgtag | aaagaacacc | tcatgttcct | tatcgagaat | ctaaactaac | tagaatcctc | 960 |
| caggattctc | ttggagggcg | tacaagaaca | tctataattg | caacaatttc | tcctgcatct | 1020 |
| ctcaatcttg | aggaaactct | gagtacattg | gaatatgctc | atagagcaaa | gaacatattg | 1080 |
| ctcgagggta | ccgagcagaa | gctgatcagc | gaggaggacc | tgatcgagca | ccaccaccac | 1140 |
| caccactga | | | | | | 1149 |

<210> SEQ ID NO 4
<211> LENGTH: 382
<212> TYPE: PRT
<213> ORGANISM: Human

<400> SEQUENCE: 4

Met Ala Cys Gln Pro Asn Ser Ser Ala Lys Lys Lys Glu Glu Lys Gly
1               5                   10                  15

Lys Asn Ile Gln Val Val Arg Cys Arg Pro Phe Asn Leu Ala Glu
            20                  25                  30

Arg Lys Ala Ser Ala His Ser Ile Val Glu Cys Asp Pro Val Arg Lys
        35                  40                  45

Glu Val Ser Val Arg Thr Gly Gly Leu Ala Asp Lys Ser Ser Arg Lys
    50                  55                  60

Thr Tyr Thr Phe Asp Met Val Phe Gly Ala Ser Thr Lys Gln Ile Asp
65                  70                  75                  80

```
Val Tyr Arg Ser Val Val Cys Pro Ile Leu Asp Glu Val Ile Met Gly
                85                  90                  95
Tyr Asn Cys Thr Ile Phe Ala Tyr Gly Gln Thr Gly Thr Gly Lys Thr
            100                 105                 110
Phe Thr Met Glu Gly Glu Arg Ser Pro Asn Glu Glu Tyr Thr Trp Glu
        115                 120                 125
Glu Asp Pro Leu Ala Gly Ile Ile Pro Arg Thr Leu His Gln Ile Phe
    130                 135                 140
Glu Lys Leu Thr Asp Asn Gly Thr Glu Phe Ser Val Lys Val Ser Leu
145                 150                 155                 160
Leu Glu Ile Tyr Asn Glu Glu Leu Phe Asp Leu Leu Asn Pro Ser Ser
                165                 170                 175
Asp Val Ser Glu Arg Leu Gln Met Phe Asp Asp Pro Arg Asn Lys Arg
            180                 185                 190
Gly Val Ile Ile Lys Gly Leu Glu Glu Ile Thr Val His Asn Lys Asp
        195                 200                 205
Glu Val Tyr Gly Ile Leu Glu Lys Gly Ala Ala Lys Arg Thr Thr Ala
    210                 215                 220
Ala Thr Leu Met Asn Ala Tyr Ser Ser Arg Ser His Ser Val Phe Ser
225                 230                 235                 240
Val Thr Ile His Met Lys Glu Thr Thr Ile Asp Gly Glu Glu Leu Val
                245                 250                 255
Lys Ile Gly Lys Leu Asn Leu Val Asp Leu Ala Gly Ser Glu Asn Ile
            260                 265                 270
Gly Arg Ser Gly Ala Val Asp Lys Arg Ala Arg Glu Ala Gly Asn Ile
        275                 280                 285
Asn Gln Ser Leu Leu Thr Leu Gly Arg Val Ile Thr Ala Leu Val Glu
    290                 295                 300
Arg Thr Pro His Val Pro Tyr Arg Glu Ser Lys Leu Thr Arg Ile Leu
305                 310                 315                 320
Gln Asp Ser Leu Gly Gly Arg Thr Arg Thr Ser Ile Ile Ala Thr Ile
                325                 330                 335
Ser Pro Ala Ser Leu Asn Leu Glu Glu Thr Leu Ser Thr Leu Glu Tyr
            340                 345                 350
Ala His Arg Ala Lys Asn Ile Leu Leu Glu Gln Thr Glu Gly Lys Leu
        355                 360                 365
Ile Ser Glu Glu Asp Leu Ile Glu His His His His His His
    370                 375                 380

<210> SEQ ID NO 5
<211> LENGTH: 1542
<212> TYPE: DNA
<213> ORGANISM: Human

<400> SEQUENCE: 5
atggcgtgcc agccaaattc gtctgcgaag aagaaagagg agaaggggaa gaacatccag      60
gtggtggtga gatgcagacc atttaatttg gcagagcgga agctagcgc ccattcaata     120 gtagaatgtg atcctgtacg aaaagaagtt agtgtacgaa ctggaggatt ggctgacaag    180
agctcaagga aaacatacac ttttgatatg gtgtttggag catctactaa acagattgat    240
gtttaccgag gtgttgtttg tccaattctg atgaagtta ttatgggcta taattgcact    300
atctttgcgt atggccaaac tggcactgga aaaacttta caatggaagg tgaaaggtca    360
cctaatgaag agtatacctg ggaagaggat cccttggctg gtataattcc acgtacccctt   420
```

-continued

```
catcaaattt tgagaaact tactgataat ggtactgaat tttcagtcaa agtgtctctg      480
ttggagatct ataatgaaga gctttttgat cttcttaatc catcatctga tgtttctgag    540
agactacaga tgtttgatga tccccgtaac aagagaggag tgataattaa aggtttagaa    600
gaaattacag tacacaacaa ggatgaagtg tatcaaattt tagaaaaggg ggcagcaaaa    660
aggacaactg cagctactct gatgaatgca tactctagtc gttcccactc agttttctct    720
gttacaatac atatgaaaga aactacgatt gatggagaag agcttgttaa aatcggaaag    780
ttgaacttgg ttgatcttgc aggaagtgaa acattggcc gttctggagc tgttgataag     840
agagctcggg aagctggaaa tataaatcaa tccctgttga ctttgggaag ggtcattact    900
gcccttgtag aaagaacacc tcatgttcct tatcgagaat ctaaactaac tagaatcctc    960
caggattctc ttggagggcg tacaagaaca tctataattg caacaatttc tcctgcatct   1020
ctcaatcttg aggaaactct gagtacattg gaatatgctc atagagcaaa gaacatattg   1080
aataagcctg aagtgaatca gaaactcacc aaaaaagctc ttattaagga gtatacggag   1140
gagatagaac gttaaaacg agatcttgct gcagcccgtg agaaaaatgg agtgtatatt    1200
tctgaagaaa attttagagt catgagtgga aaattaactg ttcaagaaga gcagattgta   1260
gaattgattg aaaaaattgg tgctgttgag gaggagctga ataggttac agagttgttt    1320 atggataata aaaatgaact tgaccagtgt aaatctgacc tgcaaaataa aacacaagaa   1380
cttgaaacca ctcaaaaaca tttgcaagaa actaaattac aacttgttaa agaagaatat   1440
atcacatcag ctttggaaag tactgaggag aaactcgagg gtaccgagca aagctgatc    1500 agcgaggagg acctgatcga gcaccaccac caccaccact ga                      1542
```

<210> SEQ ID NO 6
<211> LENGTH: 513
<212> TYPE: PRT
<213> ORGANISM: Human

<400> SEQUENCE: 6

```
Met Ala Cys Gln Pro Asn Ser Ser Ala Lys Lys Glu Glu Lys Gly
 1               5                  10                  15

Lys Asn Ile Gln Val Val Arg Cys Arg Pro Phe Asn Leu Ala Glu
                20                  25                  30

Arg Lys Ala Ser Ala His Ser Ile Val Glu Cys Asp Pro Val Arg Lys
             35                  40                  45

Glu Val Ser Val Arg Thr Gly Gly Leu Ala Asp Lys Ser Ser Arg Lys
         50                  55                  60

Thr Tyr Thr Phe Asp Met Val Phe Gly Ala Ser Thr Lys Gln Ile Asp
 65                  70                  75                  80

Val Tyr Arg Ser Val Val Cys Pro Ile Leu Asp Glu Val Ile Met Gly
                 85                  90                  95

Tyr Asn Cys Thr Ile Phe Ala Tyr Gly Gln Thr Gly Thr Gly Lys Thr
                100                 105                 110

Phe Thr Met Glu Gly Glu Arg Ser Pro Asn Glu Glu Tyr Thr Trp Glu
            115                 120                 125

Glu Asp Pro Leu Ala Gly Ile Ile Pro Arg Thr Leu His Gln Ile Phe
        130                 135                 140

Glu Lys Leu Thr Asp Asn Gly Thr Glu Phe Ser Val Lys Val Ser Leu
145                 150                 155                 160

Leu Glu Ile Tyr Asn Glu Glu Leu Phe Asp Leu Leu Asn Pro Ser Ser
                165                 170                 175
```

-continued

```
Asp Val Ser Glu Arg Leu Gln Met Phe Asp Asp Pro Arg Asn Lys Arg
            180                 185                 190
Gly Val Ile Ile Lys Gly Leu Glu Glu Ile Thr Val His Asn Lys Asp
        195                 200                 205
Glu Val Tyr Gly Ile Leu Glu Lys Gly Ala Ala Lys Arg Thr Thr Ala
    210                 215                 220
Ala Thr Leu Met Asn Ala Tyr Ser Ser Arg Ser His Ser Val Phe Ser
225                 230                 235                 240
Val Thr Ile His Met Lys Glu Thr Thr Ile Asp Gly Glu Glu Leu Val
                245                 250                 255
Lys Ile Gly Lys Leu Asn Leu Val Asp Leu Ala Gly Ser Glu Asn Ile
            260                 265                 270
Gly Arg Ser Gly Ala Val Asp Lys Arg Ala Arg Glu Ala Gly Asn Ile
        275                 280                 285
Asn Gln Ser Leu Leu Thr Leu Gly Arg Val Ile Thr Ala Leu Val Glu
    290                 295                 300
Arg Thr Pro His Val Pro Tyr Arg Glu Ser Lys Leu Thr Arg Ile Leu
305                 310                 315                 320
Gln Asp Ser Leu Gly Gly Arg Thr Arg Thr Ser Ile Ile Ala Thr Ile
                325                 330                 335
Ser Pro Ala Ser Leu Asn Leu Glu Glu Thr Leu Ser Thr Leu Glu Tyr
            340                 345                 350
Ala His Arg Ala Lys Asn Ile Leu Asn Lys Pro Glu Val Asn Gln Lys
        355                 360                 365
Leu Thr Lys Lys Ala Leu Ile Lys Glu Tyr Thr Glu Glu Ile Glu Arg
    370                 375                 380
Leu Lys Arg Asp Leu Ala Ala Ala Arg Glu Lys Asn Gly Val Tyr Ile
385                 390                 395                 400
Ser Glu Glu Asn Phe Arg Val Met Ser Gly Lys Leu Thr Val Gln Glu
                405                 410                 415
Glu Gln Ile Val Glu Leu Ile Glu Lys Ile Gly Ala Val Glu Glu Glu
            420                 425                 430
Leu Asn Arg Val Thr Glu Leu Phe Met Asp Asn Lys Asn Glu Leu Asp
        435                 440                 445
Gln Cys Lys Ser Asp Leu Gln Asn Lys Thr Gln Glu Leu Glu Thr Thr
    450                 455                 460
Gln Lys His Leu Gly Glu Thr Lys Leu Gly Leu Val Lys Glu Gly Tyr
465                 470                 475                 480
Ile Thr Ser Ala Leu Glu Ser Thr Glu Glu Lys Leu Glu Gln Thr Glu
                485                 490                 495
Gly Lys Leu Ile Ser Glu Glu Asp Leu Ile Glu His His His His His
            500                 505                 510
His
```

<210> SEQ ID NO 7
<211> LENGTH: 1728
<212> TYPE: DNA
<213> ORGANISM: Human

<400> SEQUENCE: 7

```
atggcgtgcc agccaaattc gtctgcgaag aagaaagagg agaagggaa gaacatccag      60 gtggtggtga gatgcagacc atttaatttg gcagagcgga agctagcgc ccattcaata    120 gtagaatgtg atcctgtacg aaaagaagtt agtgtacgaa ctggaggatt ggctgacaag    180
```

-continued

```
agctcaagga aaacatacac ttttgatatg gtgtttggag catctactaa acagattgat    240
gtttaccgag gtgttgtttg tccaattctg gatgaagtta ttatgggcta taattgcact    300
atctttgcgt atggccaaac tggcactgga aaaacttta caatggaagg tgaaaggtca    360
cctaatgaag agtatacctg ggaagaggat cccttggctg gtataattcc acgtacccttt    420
catcaaattt ttgagaaact tactgataat ggtactgaat tttcagtcaa agtgtctctg    480
ttggagatct ataatgaaga gctttttgat cttcttaatc catcatctga tgtttctgag    540
agactacaga tgtttgatga tccccgtaac aagagaggag tgataattaa aggtttagaa    600
gaaattacag tacacaacaa ggatgaagtg tatcaaattt tagaaaaggg ggcagcaaaa    660
aggacaactg cagctactct gatgaatgca tactctagtc gttcccactc agttttctct    720
gttacaatac atatgaaaga aactacgatt gatggagaag agcttgttaa atcggaaag    780
ttgaacttgg ttgatcttgc aggaagtgaa acattggcc gttctggagc tgttgataag    840
agagctcggg aagctggaaa tataaatcaa tccctgttga ctttgggaag ggtcattact    900
gcccttgtag aaagaacacc tcatgttcct tatcgagaat ctaaactaac tagaatcctc    960
caggattctc ttggagggcg tacaagaaca tctataattg caacaatttc tcctgcatct   1020
ctcaatcttg aggaaactct gagtacattg gaatatgctc atagagcaaa gaacatattg   1080
aataagcctg aagtgaatca gaaactcacc aaaaaagctc ttattaagga gtatacggag   1140
gagatagaac gttaaaaacg agatcttgct gcagcccgtg agaaaaatgg agtgtatatt   1200
tctgaagaaa attttagagt catgagtgga aaattaactg ttcaagaaga gcagattgta   1260
gaattgatta aaaaaattgg tgctgttgag gaggagctga ataggttac agagttgttt    1320
atggataata aaaatgaact tgaccagtgt aaatctgacc tgcaaaataa aacacaagaa   1380
cttgaaacca ctcaaaaaca tttgcaagaa actaaattac aacttgttaa agaagaatat   1440
atcacatcag cttggaaag tactgaggag aaacttcatg atgctgccag caagctgctt   1500
aacacagttg aagaaactac aaaagatgta tctggtctcc attccaaact ggatcgtaag   1560
aaggcagttg accaacacaa tgcagaagct caggatattt ttggcaaaaa cctgaatagt   1620
ctgtttaata atatgaaaga attaattaag gatggcagcc tcgagggtac cgagcagaag   1680
ctgatcagcg aggaggacct gatcgagcac caccaccacc accactga                1728
```

<210> SEQ ID NO 8
<211> LENGTH: 575
<212> TYPE: PRT
<213> ORGANISM: Human

<400> SEQUENCE: 8

```
Met Ala Cys Gln Pro Asn Ser Ser Ala Lys Lys Glu Glu Lys Gly
 1               5                  10                  15

Lys Asn Ile Gln Val Val Arg Cys Arg Pro Phe Asn Leu Ala Glu
                20                  25                  30

Arg Lys Ala Ser Ala His Ser Ile Val Glu Cys Asp Pro Val Arg Lys
            35                  40                  45

Glu Val Ser Val Arg Thr Gly Gly Leu Ala Asp Lys Ser Ser Arg Lys
        50                  55                  60

Thr Tyr Thr Phe Asp Met Val Phe Gly Ala Ser Thr Lys Gln Ile Asp
65                  70                  75                  80

Val Tyr Arg Ser Val Val Cys Pro Ile Leu Asp Glu Val Ile Met Gly
                85                  90                  95
```

-continued

```
Tyr Asn Cys Thr Ile Phe Ala Tyr Gly Gln Thr Gly Thr Gly Lys Thr
                100                 105                 110
Phe Thr Met Glu Gly Glu Arg Ser Pro Asn Glu Glu Tyr Thr Trp Glu
            115                 120                 125
Glu Asp Pro Leu Ala Gly Ile Ile Pro Arg Thr Leu His Gln Ile Phe
        130                 135                 140
Glu Lys Leu Thr Asp Asn Gly Thr Glu Phe Ser Val Lys Val Ser Leu
145                 150                 155                 160
Leu Glu Ile Tyr Asn Glu Glu Leu Phe Asp Leu Leu Asn Pro Ser Ser
                165                 170                 175
Asp Val Ser Glu Arg Leu Gln Met Phe Asp Asp Pro Arg Asn Lys Arg
            180                 185                 190
Gly Val Ile Ile Lys Gly Leu Glu Glu Ile Thr Val His Asn Lys Asp
        195                 200                 205
Glu Val Tyr Gly Ile Leu Glu Lys Gly Ala Ala Lys Arg Thr Thr Ala
    210                 215                 220
Ala Thr Leu Met Asn Ala Tyr Ser Ser Arg Ser His Ser Val Phe Ser
225                 230                 235                 240
Val Thr Ile His Met Lys Glu Thr Thr Ile Asp Gly Glu Glu Leu Val
                245                 250                 255
Lys Ile Gly Lys Leu Asn Leu Val Asp Leu Ala Gly Ser Glu Asn Ile
            260                 265                 270
Gly Arg Ser Gly Ala Val Asp Lys Arg Ala Arg Glu Ala Gly Asn Ile
        275                 280                 285
Asn Gln Ser Leu Leu Thr Leu Gly Arg Val Ile Thr Ala Leu Val Glu
    290                 295                 300
Arg Thr Pro His Val Pro Tyr Arg Glu Ser Lys Leu Thr Arg Ile Leu
305                 310                 315                 320
Gln Asp Ser Leu Gly Gly Arg Thr Arg Thr Ser Ile Ile Ala Thr Ile
                325                 330                 335
Ser Pro Ala Ser Leu Asn Leu Glu Glu Thr Leu Ser Thr Leu Glu Tyr
            340                 345                 350
Ala His Arg Ala Lys Asn Ile Leu Asn Lys Pro Glu Val Asn Gln Lys
        355                 360                 365
Leu Thr Lys Lys Ala Leu Ile Lys Glu Tyr Thr Glu Glu Ile Glu Arg
    370                 375                 380
Leu Lys Arg Asp Leu Ala Ala Ala Arg Glu Lys Asn Gly Val Tyr Ile
385                 390                 395                 400
Ser Glu Glu Asn Phe Arg Val Met Ser Gly Lys Leu Thr Val Gln Glu
                405                 410                 415
Glu Gln Ile Val Glu Leu Ile Glu Lys Ile Gly Ala Val Glu Glu Glu
            420                 425                 430
Leu Asn Arg Val Thr Glu Leu Phe Met Asp Asn Lys Asn Glu Leu Asp
        435                 440                 445
Gln Cys Lys Ser Asp Leu Gln Asn Lys Thr Gln Glu Leu Glu Thr Thr
    450                 455                 460
Gln Lys His Leu Gly Glu Thr Lys Leu Gly Leu Val Lys Glu Glu Tyr
465                 470                 475                 480
Ile Thr Ser Ala Leu Glu Ser Thr Glu Glu Lys Leu His Asp Ala Ala
                485                 490                 495
Ser Lys Leu Leu Asn Thr Val Glu Glu Thr Thr Lys Asp Val Ser Gly
            500                 505                 510
Leu His Ser Lys Leu Asp Arg Lys Lys Ala Val Asp Gln His Asn Ala
```

```
            515               520               525
Glu Ala Gln Asp Ile Phe Gly Lys Asn Leu Asn Ser Leu Phe Asn Asn
        530               535               540

Met Glu Glu Leu Ile Lys Asp Gly Ser Leu Gln Thr Glu Gly Lys
545                 550               555               560

Leu Ile Ser Glu Glu Asp Leu Ile Glu His His His His His His
                565               570               575
```

<210> SEQ ID NO 9
<211> LENGTH: 1107
<212> TYPE: DNA
<213> ORGANISM: Human

<400> SEQUENCE: 9

```
atggcgtgcc agccaaattc gtctgcgaag aagaaagagg agaagggaa gaacatccag      60
gtggtggtga gatgcagacc atttaatttg gcagagcgga agctagcgc ccattcaata     120
gtagaatgtg atcctgtacg aaaagaagtt agtgtacgaa ctggaggatt ggctgacaag    180
agctcaagga aacatacac ttttgatatg gtgtttggag catctactaa acagattgat     240
gtttaccgag gtgttgtttg tccaattctg gatgaagtta ttatgggcta taattgcact    300
atctttgcgt atggccaaac tggcactgga aaaacttttta caatgaagg tgaaaggtca    360
cctaatgaag agtatacctg ggaagaggat ccccttggctg gtataattcc acgtaccctt   420
catcaaattt tgagaaaact tactgataat ggtactgaat tttcagtcaa agtgtctctg    480
ttggagatct ataatgaaga gcttttgat cttcttaatc catcatctga tgtttctgag    540
agactacaga tgtttgatga tccccgtaac aagagaggag tgataattaa aggtttagaa    600
gaaattacag tacacaacaa ggatgaagtg tatcaaattt tagaaaaggg ggcagcaaaa    660
aggacaactg cagctactct gatgaatgca tactctagtc gttccccactc agttttctct    720
gttacaatac atatgaaaga aactacgatt gatggagaag agcttgttaa atcggaaag     780
ttgaacttgg ttgatcttgc aggaagtgaa acattggcc gttctggagc tgttgataag    840
agagctcggg aagctggaaa tataaatcaa tccctgttga ctttgggaag ggtcattact    900
gcccttgtag aaagaacacc tcatgttcct tatcgagaat ctaaactaac tagaatcctc    960
caggattctc ttggagggcg tacaagaaca tctataattg caacaatttc tcctgcatct   1020
ctcaatcttg aggaaactct gagtacattg gaatatgctc atagagcaaa gaacatattg   1080
aataagcctg aagtgaatca gaaatag                                        1107
```

<210> SEQ ID NO 10
<211> LENGTH: 368
<212> TYPE: PRT
<213> ORGANISM: Human

<400> SEQUENCE: 10

```
Met Ala Cys Gln Pro Asn Ser Ser Ala Lys Lys Lys Glu Glu Lys Gly
  1               5                  10                  15

Lys Asn Ile Gln Val Val Arg Cys Arg Pro Phe Asn Leu Ala Glu
             20                  25                  30

Arg Lys Ala Ser Ala His Ser Ile Val Glu Cys Asp Pro Val Arg Lys
             35                  40                  45

Glu Val Ser Val Arg Thr Gly Gly Leu Ala Asp Lys Ser Ser Arg Lys
         50                  55                  60

Thr Tyr Thr Phe Asp Met Val Phe Gly Ala Ser Thr Lys Gln Ile Asp
 65                  70                  75                  80
```

```
Val Tyr Arg Ser Val Val Cys Pro Ile Leu Asp Glu Val Ile Met Gly
            85                  90                  95
Tyr Asn Cys Thr Ile Phe Ala Tyr Gly Gln Thr Gly Thr Gly Lys Thr
            100                 105                 110
Phe Thr Met Glu Gly Glu Arg Ser Pro Asn Glu Glu Tyr Thr Trp Glu
            115                 120                 125
Glu Asp Pro Leu Ala Gly Ile Ile Pro Arg Thr Leu His Gln Ile Phe
        130                 135                 140
Glu Lys Leu Thr Asp Asn Gly Thr Glu Phe Ser Val Lys Val Ser Leu
145                 150                 155                 160
Leu Glu Ile Tyr Asn Glu Glu Leu Phe Asp Leu Leu Asn Pro Ser Ser
                165                 170                 175
Asp Val Ser Glu Arg Leu Gln Met Phe Asp Asp Pro Arg Asn Lys Arg
                180                 185                 190
Gly Val Ile Ile Lys Gly Leu Glu Glu Ile Thr Val His Asn Lys Asp
            195                 200                 205
Glu Val Tyr Gly Ile Leu Glu Lys Gly Ala Ala Lys Arg Thr Thr Ala
        210                 215                 220
Ala Thr Leu Met Asn Ala Tyr Ser Ser Arg Ser His Ser Val Phe Ser
225                 230                 235                 240
Val Thr Ile His Met Lys Glu Thr Thr Ile Asp Gly Glu Glu Leu Val
                245                 250                 255
Lys Ile Gly Lys Leu Asn Leu Val Asp Leu Ala Gly Ser Glu Asn Ile
                260                 265                 270
Gly Arg Ser Gly Ala Val Asp Lys Arg Ala Arg Glu Ala Gly Asn Ile
            275                 280                 285
Asn Gln Ser Leu Leu Thr Leu Gly Arg Val Ile Thr Ala Leu Val Glu
        290                 295                 300
Arg Thr Pro His Val Pro Tyr Arg Glu Ser Lys Leu Thr Arg Ile Leu
305                 310                 315                 320
Gln Asp Ser Leu Gly Gly Arg Thr Arg Thr Ser Ile Ile Ala Thr Ile
                325                 330                 335
Ser Pro Ala Ser Leu Asn Leu Glu Glu Thr Leu Ser Thr Leu Glu Tyr
                340                 345                 350
Ala His Arg Ala Lys Asn Ile Leu Asn Lys Pro Glu Val Asn Gln Lys
        355                 360                 365
```